US009974466B2

(12) United States Patent
Kimmel

(10) Patent No.: US 9,974,466 B2
(45) Date of Patent: May 22, 2018

(54) METHOD AND APPARATUS FOR DETECTING CHANGE IN HEALTH STATUS

(71) Applicant: Zebadiah M. Kimmel, Cambridge, MA (US)

(72) Inventor: Zebadiah M. Kimmel, Cambridge, MA (US)

(73) Assignee: Atlas5D, Inc., Cambridge, MA (US)

( * ) Notice: Subject to any disclaimer, the term of this patent is extended or adjusted under 35 U.S.C. 154(b) by 842 days.

(21) Appl. No.: 14/352,305

(22) PCT Filed: Oct. 3, 2012

(86) PCT No.: PCT/US2012/058534
§ 371 (c)(1),
(2) Date: Apr. 16, 2014

(87) PCT Pub. No.: WO2013/058985
PCT Pub. Date: Apr. 25, 2013

(65) Prior Publication Data
US 2014/0243686 A1 Aug. 28, 2014

Related U.S. Application Data

(60) Provisional application No. 61/548,079, filed on Oct. 17, 2011, provisional application No. 61/561,627, (Continued)

(51) Int. Cl.
A61B 5/11 (2006.01)
A61B 5/00 (2006.01)
G06F 19/00 (2018.01)

(52) U.S. Cl.
CPC .......... A61B 5/1113 (2013.01); A61B 5/0013 (2013.01); A61B 5/1114 (2013.01);
(Continued)

(58) Field of Classification Search
CPC combination set(s) only.
See application file for complete search history.

(56) References Cited

U.S. PATENT DOCUMENTS 4,406,544 A 9/1983 Takada et al.
4,650,330 A 3/1987 Fujita
(Continued)

FOREIGN PATENT DOCUMENTS

WO WO-01/001354 A1 1/2001
WO WO-2013/058985 A1 4/2013
WO WO-2014/112632 A1 7/2014

OTHER PUBLICATIONS

Stone et al. ("Evaluation of an Inexpensive Depth Camera for Passive In-Home Fall Risk Assessment", 2011, 5th International Conference on Pervasive Computing Technologies for Healthcare (PervasiveHealth) and Workshops, pp. 71-77).*
(Continued)

Primary Examiner — Serkan Akar
Assistant Examiner — Farshad Negarestan
(74) Attorney, Agent, or Firm — Choate, Hall & Stewart LLP; William R. Haulbrook

(57) ABSTRACT

A system for early warning of health status decline includes at least one energy emitter configured to emit energy onto a field-of-view that contains an individual, and at least one energy sensor configured to capture reflected energy from within the field-of-view. A spatial measurement module calculates spatial measurements of a surface portion of the body of the individual when the individual is either stationary or moving about in real-time, based on data from the energy sensor. A comparator module detects deviations in measurements from baseline values indicative of a deterioration in health status of the individual.

26 Claims, 24 Drawing Sheets

Related U.S. Application Data filed on Nov. 18, 2011, provisional application No. 61/567,940, filed on Dec. 7, 2011.

(52) U.S. Cl.
CPC ........ *A61B 5/1118* (2013.01); *G06F 19/3418* (2013.01); *G16H 50/30* (2018.01)

(56) References Cited

U.S. PATENT DOCUMENTS

| | | | |
|---|---|---|---|
| 5,530,652 | A | 6/1996 | Croyle et al. |
| 5,742,521 | A | 4/1998 | Ellenby et al. |
| 6,111,755 | A | 8/2000 | Park |
| 7,440,590 | B1 | 10/2008 | Hassebrook et al. |
| 7,551,432 | B1 | 6/2009 | Bockheim et al. |
| 7,684,185 | B2 | 3/2010 | Farrugia |
| 8,269,834 | B2 | 9/2012 | Albertson et al. |
| 8,613,666 | B2 | 12/2013 | Esaki et al. |
| 8,639,020 | B1 | 1/2014 | Kutliroff et al. |
| 8,775,710 | B1 | 7/2014 | Miller et al. |
| 8,787,663 | B2 | 7/2014 | Litvak et al. |
| 8,902,607 | B1 | 12/2014 | Chang et al. |
| 9,037,354 | B2 | 5/2015 | Mondragon et al. |
| 9,189,886 | B2 | 11/2015 | Black et al. |
| 9,341,464 | B2 | 5/2016 | Kimmel |
| 9,361,696 | B2 | 6/2016 | Allezard et al. |
| 9,393,695 | B2 | 7/2016 | Scott et al. |
| 9,513,667 | B2 | 12/2016 | Pais et al. |
| 9,520,072 | B2 | 12/2016 | Sun et al. |
| 9,524,554 | B2 | 12/2016 | Plagge et al. |
| 9,600,993 | B2 | 3/2017 | Kimmel |
| 2003/0076414 | A1 | 4/2003 | Sato et al. |
| 2003/0209893 | A1 | 11/2003 | Breed et al. |
| 2003/0231788 | A1 | 12/2003 | Yukhin et al. |
| 2004/0083142 | A1 | 4/2004 | Kozzinn |
| 2004/0104905 | A1 | 6/2004 | Chung et al. |
| 2004/0236456 | A1 | 11/2004 | Pieper et al. |
| 2005/0094879 | A1* | 5/2005 | Harville ............. G06K 9/00201 382/209 |
| 2005/0162824 | A1 | 7/2005 | Thompson |
| 2006/0252541 | A1 | 11/2006 | Zalewski et al. |
| 2007/0229850 | A1 | 10/2007 | Herber |
| 2007/0252831 | A1 | 11/2007 | Lind et al. |
| 2008/0103637 | A1 | 5/2008 | Bliven et al. |
| 2009/0244309 | A1 | 10/2009 | Maison et al. |
| 2010/0007717 | A1 | 1/2010 | Spektor et al. |
| 2010/0049095 | A1* | 2/2010 | Bunn ................... A61B 5/1038 600/595 |
| 2010/0172567 | A1 | 7/2010 | Prokoski |
| 2010/0191541 | A1 | 7/2010 | Prokoski |
| 2010/0226533 | A1 | 9/2010 | Bharath et al. |
| 2011/0052006 | A1 | 3/2011 | Gurman et al. |
| 2011/0193939 | A1 | 8/2011 | Vassigh et al. |
| 2011/0205337 | A1 | 8/2011 | Ganapathi et al. |
| 2011/0206273 | A1 | 8/2011 | Plagemann et al. |
| 2011/0211044 | A1 | 9/2011 | Shpunt et al. |
| 2011/0211754 | A1 | 9/2011 | Litvak et al. |
| 2011/0288964 | A1 | 11/2011 | Linder et al. |
| 2011/0298801 | A1 | 12/2011 | Wexler et al. |
| 2012/0046101 | A1 | 2/2012 | Marks et al. |
| 2012/0076361 | A1 | 3/2012 | Fujiyoshi |
| 2012/0120580 | A1 | 5/2012 | Yukawa et al. |
| 2012/0128327 | A1 | 5/2012 | Matsubara |
| 2012/0159290 | A1 | 6/2012 | Pulsipher et al. |
| 2012/0162483 | A1 | 6/2012 | Sutton et al. |
| 2012/0229634 | A1 | 9/2012 | Laett et al. |
| 2012/0242501 | A1 | 9/2012 | Tran et al. |
| 2012/0257814 | A1 | 10/2012 | Kohli et al. |
| 2012/0269384 | A1 | 10/2012 | Jones et al. |
| 2012/0326959 | A1 | 12/2012 | Murthi et al. |
| 2013/0048722 | A1* | 2/2013 | Davis ................. G06K 7/10861 235/383 |
| 2013/0109253 | A1 | 5/2013 | Gammon et al. |
| 2013/0163170 | A1 | 6/2013 | Chen |
| 2013/0163879 | A1 | 6/2013 | Katz et al. |
| 2013/0315475 | A1 | 11/2013 | Song et al. |
| 2013/0335235 | A1 | 12/2013 | Carr et al. |
| 2014/0163330 | A1 | 6/2014 | Horseman |
| 2014/0243686 | A1 | 8/2014 | Kimmel |
| 2014/0279740 | A1 | 9/2014 | Wernevi et al. |
| 2014/0298379 | A1 | 10/2014 | Singh |
| 2014/0299775 | A1 | 10/2014 | Kimmel |
| 2014/0300907 | A1 | 10/2014 | Kimmel |
| 2014/0376172 | A1 | 12/2014 | Love et al. |
| 2015/0000025 | A1 | 1/2015 | Clements |
| 2015/0213702 | A1 | 7/2015 | Kimmel |
| 2015/0325004 | A1 | 11/2015 | Utsunomiya et al. |
| 2015/0331463 | A1 | 11/2015 | Obie et al. |
| 2016/0231778 | A1 | 8/2016 | Kaneko |
| 2016/0247017 | A1 | 8/2016 | Sareen et al. |
| 2016/0266607 | A1 | 9/2016 | Varsanik et al. |
| 2016/0267652 | A1 | 9/2016 | Kimmel et al. |
| 2016/0331277 | A1 | 11/2016 | Kimmel |

OTHER PUBLICATIONS

Loker et al., "Size-specific Analysis of Body Scan Data to Improve Apparel Fit," Journal of Textile and Apparel, Technology and Management, 4(3): 4-6 (2005).

Viktor et al., "Measuring to Fit: Virtual Tailoring through Cluster Analysis and Classification," NRC Publications Archive, entire document (2006).

International Search Report for PCT/US12/58534 dated Feb. 5, 2013 (2 pages).

Written Opinion for PCT/US12/58534 dated Feb. 5, 2013 (5 pages).

Ergotron Dock Locker, dated Feb. 6, 2015, <http://www.hpi.com/ergotron-dock-locker-secure-table-stand.html> retrieved from google on Jan. 6, 2017.

* cited by examiner

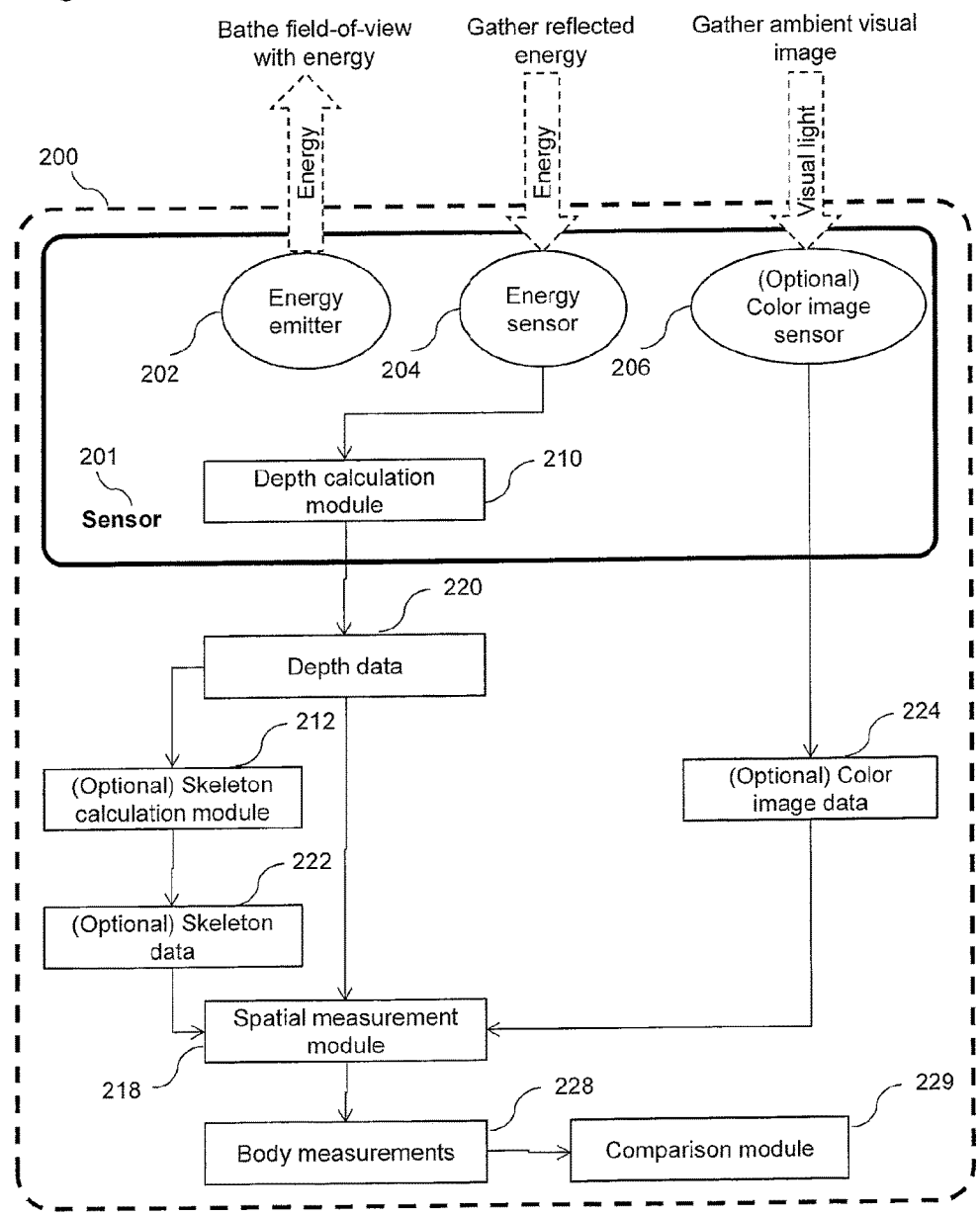

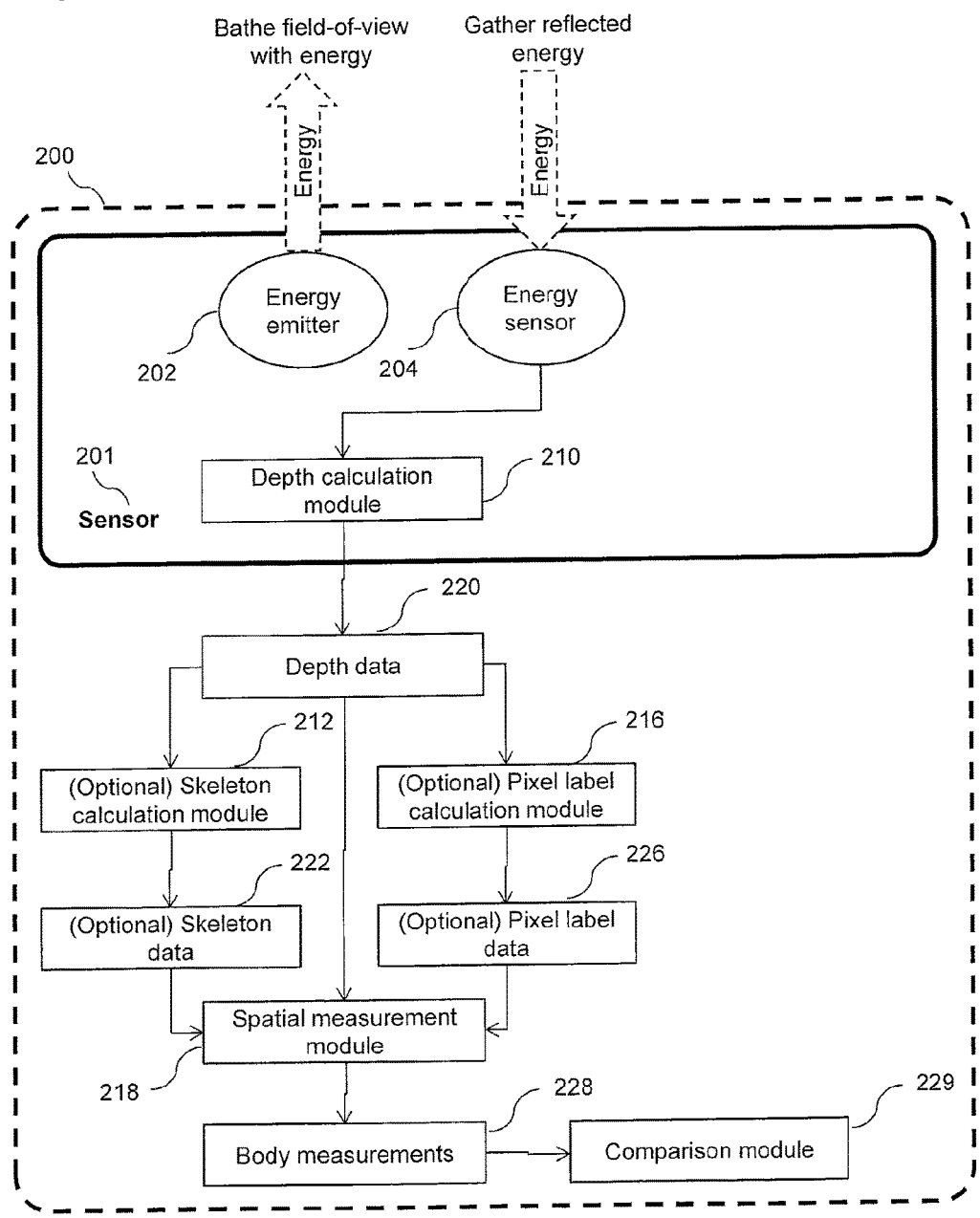

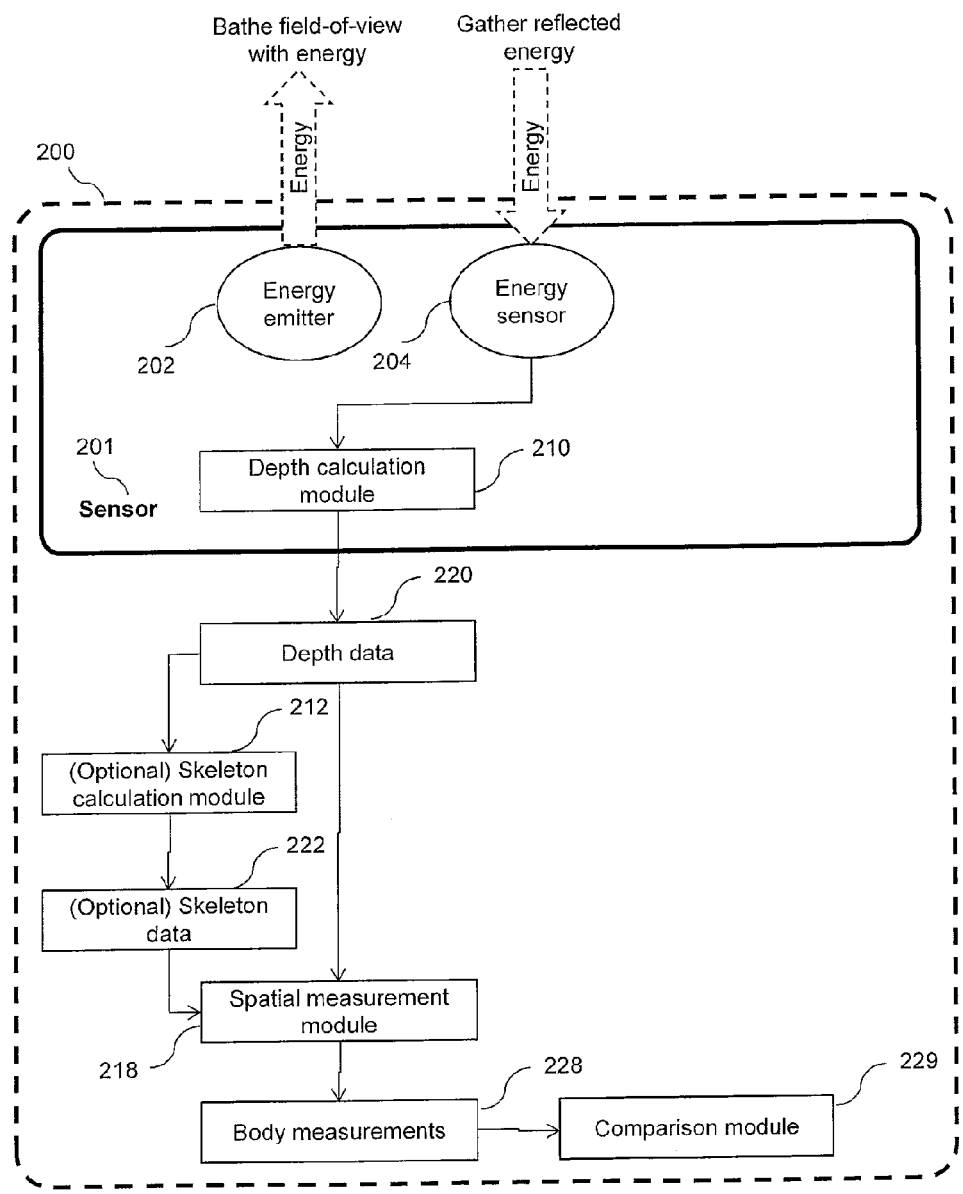

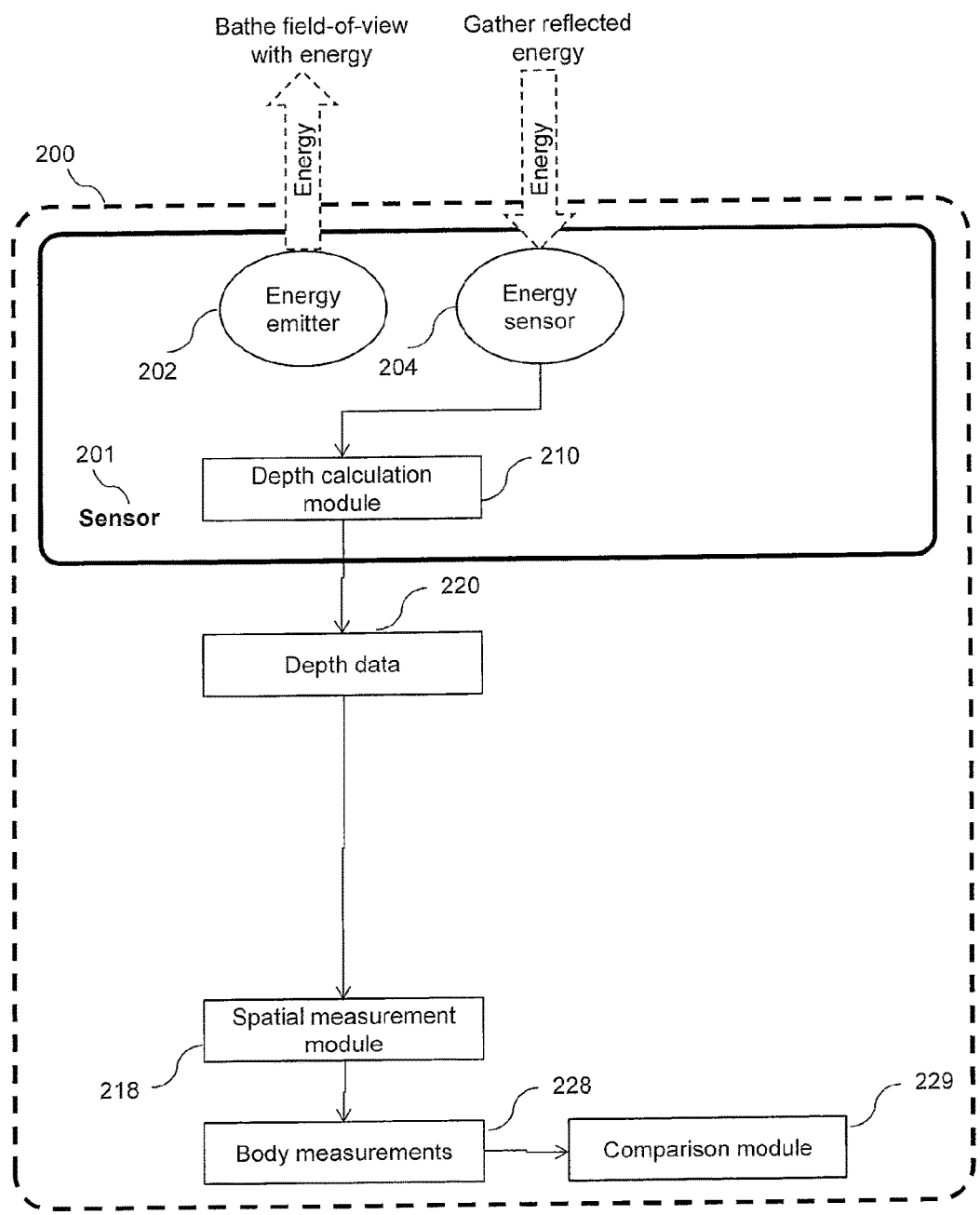

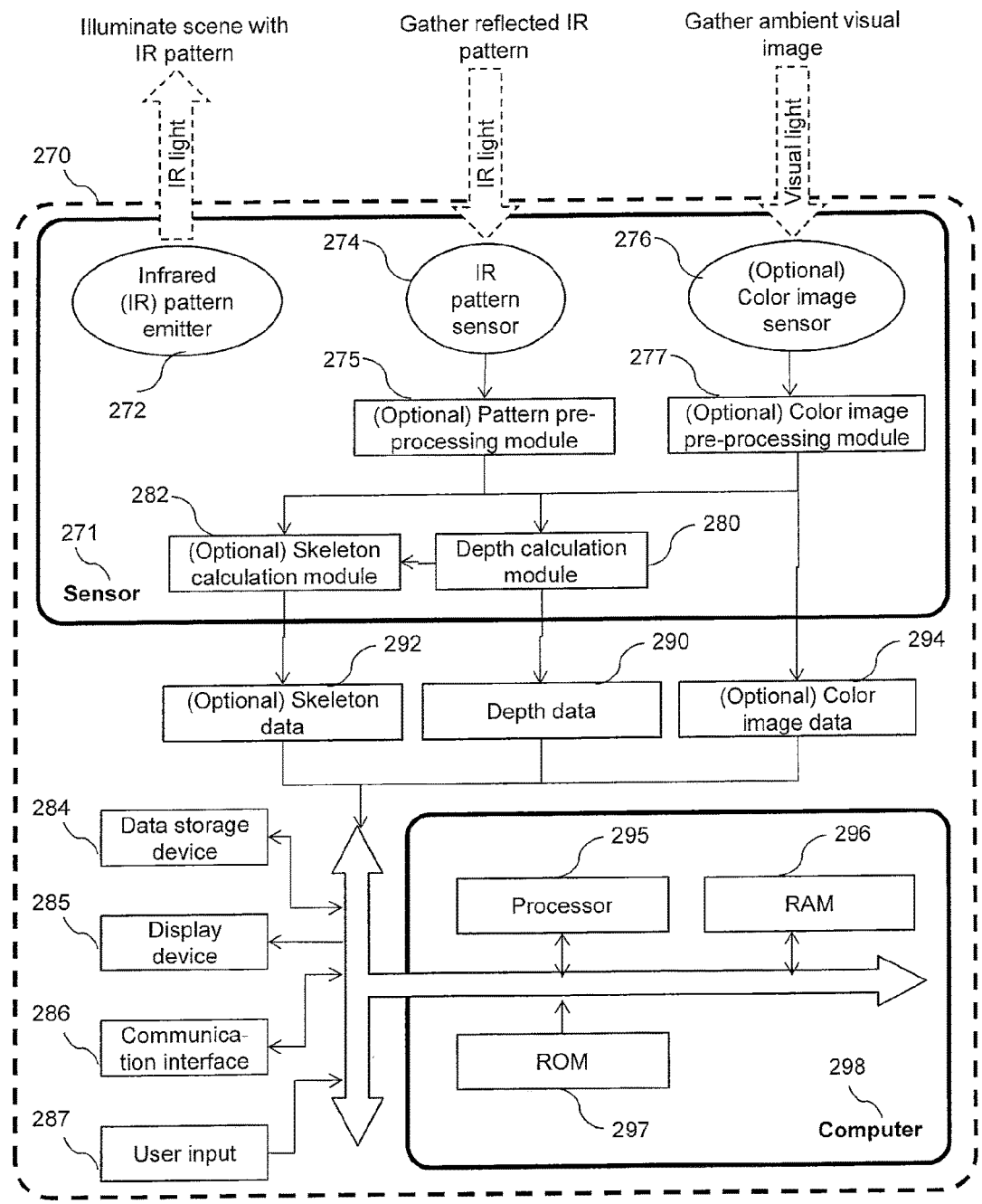

Figure 4

| Measurement | Preferred profile | Alternate profile |
| --- | --- | --- |
| • Angle of body relative to horizontal (left- or right-leaning) | • Front | • Back |
| • Angle of body relative to horizontal (forward- or backward-leaning) | • Side | • (None) |
| • Angle of head-and-neck relative to torso | • Side | • (None) |
| • Angle of torso relative to legs | • Side | • (None) |
| • Position of hand relative to shoulder | • Front | • Side |
| • Position of hand relative to other hand | • Front | • (None) |
| • Position of knee relative to hip | • Side | • Front |
| • Position of knee relative to other knee | • Front | • Back |
| • Tip of foot | • Side | • Any |
| • Back of heel | • Side | • Any |
| • Bottom of sole of foot | • Side | • Any |
| • Position of foot relative to hip | • Side | • Front |
| • Position of foot relative to other foot | • Side | • Front |
| • Position of head relative to floor | • Front | • Any |
| • Volume of speech | • Front | • Any |
| • Timbre of speech | • Front | • Any |

Figure 17

| Derivative measurement | Preferred profile | Alternate profile |
| --- | --- | --- |
| • Rotation of upper body relative to lower body | • Front | • Side |
| • Maximum distance between the two feet during a stride | • Side | • Front or Back |
| • Maximum distance between hand and torso during a stride | • Side | • Front or Back |
| • Maximum angle of rotation at the shoulder joint during a stride | • Side | • Front or Back |
| • Speed of locomotion | • Side | • Any |
| • Stride distance of locomotion | • Side | • Front or Back |
| • Frequency of locomotion | • Side | • Any |
| • Average / maximum acceleration of hand or foot | • Side | • Front or Back |
| • Qualitative estimate of stance | • Front | • Back |
| • Frequency of speech | • Front | • Any |
| • Time per day spent standing | • Front or Side | • Any |
| • Time per day spent walking | • Front or Side | • Any |
| • Time per day spent sitting | • Front | • Any |

METHOD AND APPARATUS FOR DETECTING CHANGE IN HEALTH STATUS

PRIORITY CLAIM

This application claims the benefit of Provisional Patent Application Ser. No. 61/548,079, filed on Oct. 17, 2011, Provisional Patent Application Ser. No. 61/561,627, filed on Nov. 18, 2011, and Provisional Patent Application Ser. No. 61/567,940, filed on Dec. 7, 2011. All of the above-identified provisional patent applications are incorporated by reference herein in their entirety.

BACKGROUND OF THE INVENTION

This invention relates to early detection that a person's health status is declining, especially for aged individuals. "Health status" as used herein refers to an individual's present-day level of overall wellness, relative to that same individual's baseline (that is, typical day-to-day level) of wellness. Components of health status may include both physical components, such as physical function or bodily pain, and mental components, such as cognitive function or emotional state.

Early detection of declining health status is especially important in the aged population, driving both societal and economic benefits. On the societal dimension, early detection of declining health status can be an enabler of early intervention, which can in turn lead to more robust health of the affected individuals, greater dignity, and reduced pain and suffering—not just in the aged population, but in the population of supporting caregivers. On the economic dimensions, early detection of declining health status can be an enabler to keeping elderly individuals in their own home and out of institutional care, such as hospitals and nursing homes—which are suppliers of labor-intensive round-the-clock or intensive care, and so are far more expensive than at-home care.

Studies in the geriatric population indicate that mobility problems in the elderly are predictive of near-term disability and injuries (such as falls and fractures). For example, consistent changes in aspects of an individual's gait—such as reduced speed of walking, or reduced step length—are considered to indicate an increased risk of falling. As another example, a generalized reduction in activity level—manifested by, for example, less time each day walking around—may be predictive of early functional deterioration in a disease state (such as worsened congestive heart failure) or of an occult infection (such as pneumonia).

In general, non-transient changes in a person's activity and behavior from baseline may be predictive of imminent deterioration of that person's health status. Accordingly, many schemes have been proposed to detect such changes, and to flag them to caregivers (such as sons and daughters) or to providers (such as nurses and doctors) for possible early intervention.

Personal Emergency Response Systems (PERS) are a widespread, commercially-available class of devices. One example of a PERS device is the Lifeline, manufactured by Philips. PERS devices typically consist of a button that is worn by the individual on a necklace or similar strap; in case of a fall or other emergency event, the individual presses the button to call for help. Some of these devices additionally carry an accelerometer, which can detect when a fall has occurred, and can call for help automatically in case the individual has been incapacitated by the fall and cannot press the button. While very useful, and potentially even life-saving, in the event of an emergency, PERS devices uniformly suffer from one critical deficiency: it is not possible for them to provide any predictive warning before an event, such as a fall, actually occurs. They can only provide early warning after the event has already taken place.

Besides PERS, a number of schemes have been proposed for early detection that an event has occurred. For example, U.S. Pat. No. 7,567,200 to Osterweil describes the use of radar to detect a fall event. As with PERS, all such events cannot provide predictive warning in advance of an event, only warning once the event has already occurred.

A number of schemes for predictive warning of event, such as a fall, involve the wearing of accelerometers or gyroscopes. For example, U.S. Pat. No. 6,895,341 to Barrey describes the use of accelerometers, worn in e.g., a semi-elastic waistband, in order to detect irregularities in an individual's locomotion. Accelerometer-based predictive methods all suffer from one critical drawback, however: they require the individual to physically carry or wear one or more accelerometers, which devices are bulky, cumbersome, uncomfortable, and embarrassing.

Other schemes for predictive warning of an event, such as a fall, rely on detecting vibrations through a floor. For example, U.S. Pat. No. 7,857,771 to Alwan describes the use of floor vibrations to passively detect different types of gait as well as actual falls. Such methods suffer from multiple deficiencies: for example, they cannot readily distinguish between multiple individuals (i.e., cannot assign a particular gait to a particular person), are subject to confounders (such as the presence of visitors, or the local condition of the floor, furniture, or building), and their input data are limited to a single, poorly informative, and noisy signal, thus limiting their accuracy and utility.

Other schemes for predictive warning of an event, such as a fall, rely on establishing an array of motion sensors throughout an area. These motion sensors may or may not require transponders to be worn. For example, U.S. Pat. No. 7,978,085 to Kearns describes the use of trackable transponders, worn by an individual, to monitor activity levels over time.

Other methods establish a network of motion sensors around an individual's home, which are capable of detecting that someone is nearby, and of measuring transition from one part of the home to another. Yet other methods may establish a network of device transducers linked to specific devices in an individual's home, such as toilet or door handles, that send a signal when the linked devices are used. Examples of companies that manufacture or sell either motion or device transducer sensors include Grand Care Systems, CareInnovations, and BeClose.

For example, U.S. Pat. No. 8,035,526 to Needham describes the use of proximity gradients to detect the presence of an individual and to supply text notification messages to that individual upon such detection. As another example, GPS-based devices are commercially available that can track the location of an individual. All motion-detection or device-transducer methods suffer from multiple deficiencies: for example, they cannot readily distinguish between multiple individuals, they may be vulnerable to interference by local furniture, buildings, or other objects, and their input data are limited to low-information streams that can detect only gross measures of motion or the occurrence of particular events (e.g., toilet flush), not more-precise and informative measures such as gait or posture or generalized activity.

Other schemes for predictive warning of declining health status are disease-specific, and so rely on measuring disease-specific parameters. For example, there are a wide variety of commercially-available devices, such as weight scales, glucometers, peak flow meters, and so on, that measure physiologic or biomarker parameters that are specific to corresponding diseases, such as congestive heart failure, diabetes, or asthma. These schemes are often highly effective in aiding management of the specific disease that they target: however, they are ineffective outside of the province of that disease (for example, no devices appear to yet exist that can provide early warning of pneumonia or dementia), and they are unable to provide early warning of a general deterioration of health status.

Other schemes for predictive warning of declining health status measure aspects of an individual's so-called Activities of Daily Living (ADL's), such as cooking a meal or balancing a checkbook or taking a medication. These schemes incorporate a wide array of devices to monitor specific aspects of ADLs: for example, electronic pillboxes or bottle caps that record whether and when a medication was retrieved by the individual (and, presumably, subsequently taken).

For example, U.S. Pat. No. 7,847,682 to Jung describes the tracking of gross behaviors, such as sleeping, eating, or exercising in order to sense abnormal changes in such behaviors. ADL-based schemes may be effective in tracking adherence to a particular type of desirable behavior, but in general, their information content is too limited to be able to draw conclusions or to provide warnings about overall health status deterioration, and are also subject to confounders.

Other schemes combine aspects of one or more of the aforementioned schemes. For example, US Patent Publication US 2011-0264008 to Yang describes the use of electromyography, accelerometers, and gyroscopes, in order to distinguish an emergency event (such as a fall) from a normal event (such as an ADL). Such combinations fail to overcome the individual deficiencies of each scheme, because the capabilities of all the aforementioned schemes, even considered in aggregate, fail to target or compensate for the root causes of their cumulative deficiencies.

Overall, known methods of early warning of declining health status suffer from one or more of the following disadvantages:

Known methods may require that devices, such as accelerometers or gyroscopes, be worn by an individual;

Known methods may generate data of insufficient quality, precision, or relevancy to provide reliable early warning of declining health status;

Known methods may invade user's privacy, for example, through the use of cameras or video Known methods may be limited to a specific disease, and therefore ineffective outside the realm of that disease;

Known methods may operate only rarely or intermittently, for example, taking measurements only at certain times of day, or only when the user does a particular activity Known methods may be active (requiring the user to go out of his or her way to perform some action, such as putting on a sensor, or pressing a button on a machine) rather than passive (where the method runs continually in the background, and doesn't require the user to do anything)

Known methods may be subject to commonly-occurring confounders, such as the presence of more than one person;

Known methods may be expensive and/or complex to execute;

Known methods may require setup and/or ongoing maintenance by dedicated experts in order to function properly;

Known methods may be able to detect an event only after it has occurred, not before; in other words, they may not possess predictive power.

Known methods may not allow real-time, interactive user interfaces, or system responses to user movement or commands.

Known methods may obtain limited depth knowledge about a scene. "Depth knowledge" or "depth data", as used herein, refers to gathering information—possibly partial, or incomplete—about the spatial positions of objects in space relative to a known coordinate system. "Image knowledge" or "image data", as used herein, refers to gathering an image of a scene, which may be in, for example, visual wavelengths or in other wavelengths of the electromagnetic spectrum. "Color image knowledge" or "color image", as used herein, refers to gathering a visual image of a scene, using color wavelengths, similar to the way in which a standard digital camera gathers a visual image. The term "camera", as used herein, refers to any sensor that may gather information about the environment, especially (though not limited to) electromagnetic measurements, such as visible or infrared light. "Camera", as used herein, is thus a general-purpose term, and does not refer specifically to, nor is limited to, visual-light devices.

U.S. Patent Publication 2011-0211044 (Shpunt) teaches a method of gathering depth knowledge about an object through the use of an illumination module, which projects patterned optical radiation onto a scene, and an image capture module, which captures an image of the reflected pattern.

Image and/or depth data may be combined to identify the spatial location of specific human body portions. U.S. Patent Publication 2011-0052006 (Gurman) teaches a method of locating portions of a humanoid form using a temporal sequence of depth maps, where each depth map represents a scene as a two-dimensional matrix of pixels indicating topographic information. U.S. Patent Publication 2011-0211754 (Litvak) teaches a method which processes image and depth data in such a way that specific parts of a body, such as the head, may be identified in the image and depth data. Thus, post-processing of image and/or depth data can generate so-called "skeleton data" or "joint data", describing the approximate locations in space of specific parts of a person's body.

SUMMARY

To overcome the above-described problems, embodiments of the present invention do not rely on accelerometers, gyroscopes, or any of the variety of aforementioned low-information-content data streams. Instead, some embodiments of the inventive method and system rely on ongoing acquisition of "data-snapshots" that are each obtained from a single viewpoint, as described below, wherein each data-snapshot contains at least depth data, and preferably contains a combination of image, depth, skeleton, and/or pixel label data. Such data-snapshots are described in detail in related application Ser. Nos. 61/548,079 and 61/561,627, which are incorporated herein by reference. Such data-snapshots may optionally be supplemented by one or more audio streams in order to observe a person's voice over time.

Measurements of an individual's activity, gait, posture, presence, and/or movement, are then obtained from one or more such data-snapshots; and, optionally, measurements of an individual's voice are obtained from the audio streams. As used herein "activity" refers to a general level of activity exhibited by a person, such as moving around, standing up or sitting down, picking up items, etc. As used herein "gait" refers to a variety of measurements of how a person walks, such as the speed of walking, or length of individual steps, etc. As used herein "posture" refers to a variety of measurements of how a person's body is positioned, for example, if someone is standing up straight or bent over, etc.

As used herein "presence" refers to the knowledge that a person is located in a particular location or area, for example, standing in a living room, or seated at a kitchen table. As used herein "movement" refers to how a portion of a person's body moves, for example, if a person's arm moves smoothly during extension versus moving in a ragged or jerky fashion, or if a person walks evenly versus unsteadily across a floor. The terms "activity", "gait", "posture", "presence", and "movement" are used herein for descriptive and illustrative purposes, and may overlap in meaning. As used herein, "voice measurements" may refer to any type of measurement of a human voice, including timbre, tone, volume, etc.

Abnormal status, or changes, in activity, gait, posture, presence, movement, and/or voice—relative to baseline—may be detected and flagged in order to provide early warning of, and the opportunity to intervene preceding, a deterioration in health status. Embodiments of the present inventive method include the following advantages, which are not intended to be an exhaustive list:

- In some embodiments, it may utilize one energy emitter and one camera, in order to obtain depth data;
- In some embodiments, it may utilize one energy emitter, and two cameras of non-overlapping frequencies, in order to obtain at least depth data, and preferably depth data, image data, skeleton data (which skeleton data may be calculated from the depth and/or image data), and/or pixel label data (which pixel label data may be calculated from the depth and/or image data);
- In some embodiments, it may utilize two cameras that are substantially co-located in space, with similar angles of view onto a scene containing the individual to be measured, such that the overall hardware components easily fit onto a shelf or at the base of a television at home;
- It may conduct some individual measurements using only a single "snapshot" of data in some embodiments; and further, may conduct more than one measurement on the same snapshot; so that the entire measurement process is carried out very rapidly;
- It does not require the individual being observed to wear any sensors or devices or special clothing;
- In some embodiments, it may operate in the dark (without the need for exogenous light);
- In some embodiments, it may operate on an ongoing basis, for example, around-the-clock;
- In some embodiments, it may not require the use of visual-light camera or video, protecting the user's privacy so that, for example, it is not possible to view the user's face or what the viewer is wearing;
- It acquires detailed, high-resolution data that are highly relevant to establishing early changes in baseline for a variety of parameters that may indicate health status deterioration, and in this way, offers early warning and predictive value before an event actually occurs;
- It does not require a separate human operator (other than the individual who is being monitored);
- It is low-cost, compact, portable, and affordable;
- It is easy to install and operate in an individual's own home;
- It does not require special training or skills to operate;
- It is able to supply health status measurements to third parties, such as relatives, caregivers, or clinicians, in order to enable reassurance and/or early warning and/or intervention;
- It permits the user to move about while health status measurements are being acquired, without having to pose or stay still;
- It is passive rather than active, and so does not require the user to have to remember to perform particular actions or to engage in particular activities;
- It enables real-time interactivity with the user, for example, it may adjust or respond in real-time to the user's movements, or communicate useful information (such as health status measurements displayed on a screen) to the user in real-time.

There are many useful applications of this low-cost, convenient, and predictive method and apparatus of providing early warning of health status deterioration. The following recitation of useful applications is not intended to be an exhaustive list, but merely points out the wide and divergent fields in which embodiments of the present inventive method find application.

Elderly individuals living alone at home are particularly vulnerable to subtle health status deterioration that escapes detection until too late. Such deterioration may be due to infection (e.g. pneumonia), malnutrition, depression, or myriad other causes, and may initially appear minor: e.g., a somewhat more-shuffling gait, a bit more time spent in bed each day, a softer volume of speech. But if not attended to, such deterioration may progress, steadily worsening until it reaches a "tipping point" after which the individual can no longer compensate, declines rapidly, and ends up hospitalized, permanently institutionalized, or both. Some embodiments of the present inventive method allow a small, affordable sensor to be placed within the individual's home that acts as a "silent guardian", watching over the individual's activity, gait, posture, presence, movement, and/or voice and flagging a caregiver or provider as soon as deviations from baseline become apparent.

Such a "silent guardian" offers benefits to caregivers and providers, in addition to the individuals being guarded. Currently, caregivers may endure round-the-clock concern and worry about their loved ones, such as elderly parents; embodiments of the present inventive method offer reassurance that caregivers will receive advance warning in many situations that previously would have "slipped through the cracks." Furthermore, providers, insurers, and the healthcare system overall, may benefit from the lower costs stemming from prevented events such as hospitalizations.

Embodiments of the present inventive method and apparatus may also be placed in care settings where individuals are treated more intensively but are still ambulatory, such as hospital wards, assisted-living facilities, or nursing homes. In these cases, such embodiments can provide early warning to on-site providers or care managers, reducing the need for round-the-clock human monitoring.

A critical barrier to placing health monitoring devices into the homes of individuals is potential invasion of privacy. For example, almost all older adults fiercely resist the placement of cameras, webcams, or other devices that might show them undressed, or in other embarrassing situations. Some embodiments of the present inventive method do not acquire and/or transmit visual-light images or video, in order to ensure privacy.

Many populations, not just the elderly, may benefit from the present inventive method: for example, disabled individuals, or individuals with chronic diseases, or individuals with illnesses that affect motion (such as multiple sclerosis), or children.

The above examples show that embodiments of the present inventive method and apparatus are useful in many applications across home, ambulatory, and hospital care, and for a wide variety of populations.

Specifically, one embodiment of the present inventive method includes the steps of:

a) Identifying a collection of body measurements for a user
b) Acquiring measurements of the user
c) Repeating step (b) until enough measurements for the user have been acquired to establish a baseline
d) Acquiring measurements of the user
e) If the measurements of step (d) indicate that the user has deviated from baseline, then optionally carrying out an action (such as sending an alert)
f) Repeating starting from step (d)

Another embodiment of the present method includes:

a) Identifying a collection of body measurements for a user
b) Identifying the user's current profile in the field-of-view
c) Acquiring a data-snapshot
d) Collecting a set of measurements from the snapshot
e) (Optionally) Adjusting or updating the measurements of step (d), for example, by averaging over time
f) (Optionally) Storing the measurements of steps (d) and/or (e) for use in future iterations of step (e)
g) Checking whether all measurements from step a) have been obtained to a desired level of accuracy or threshold In another embodiment, a method for detecting deterioration of health status includes capturing data corresponding to the individual moving within a field-of-view or remaining stationary for a predetermined amount of time within the field-of view, of at least one pattern emitter and one image capture device; calculating depth data for the field-of-view based on the emitted pattern and received image; and calculating one or more spatial measurements of a portion of a body surface of the individual based on the depth data for the field-of-view.

In another embodiment, a method for detecting deterioration of health status includes capturing data corresponding to the individual moving within a field-of-view or remaining stationary for a predetermined amount of time within the field-of view, of at least one pattern emitter and two image capture devices of non-overlapping frequencies; calculating depth data for the field-of-view based on the emitted pattern and received image, and receiving image data of a field-of-view from at least one of the image capture devices; and calculating one or more spatial measurements of a portion of a body surface of the individual based on the depth and image data for the field-of-view.

BRIEF DESCRIPTION OF THE DRAWINGS

FIGS. 2A-2F show block diagrams according to specific embodiments of the present system and method.

FIG. 4 shows a lookup table that matches direct measurements with their preferred and alternate profiles.

FIG. 17 shows a lookup table that matches derivative measurements with their preferred and alternate profiles.

DETAILED DESCRIPTION

Figure 1A:
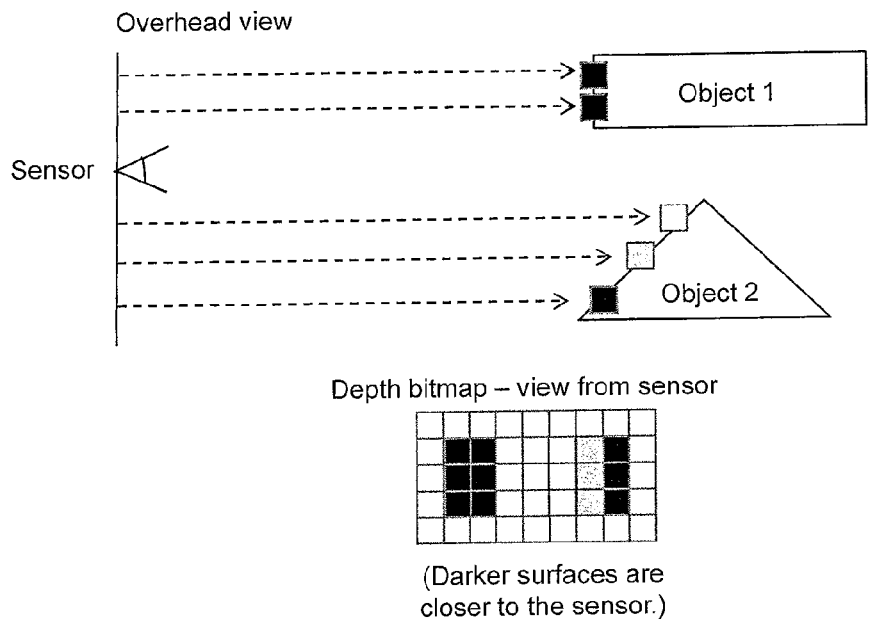
FIGS. 1A and 1B show representations of depth data.

Embodiments of the present invention are designed to automate taking physical measurements of portions of a user's body in ways that are compact, portable, private, affordable, repeatable, rapid, and convenient. The system may utilize a single energy sensor to obtain, at a minimum, depth data; or two energy sensors of non-overlapping frequencies to obtain a combination of depth data and spectral data (for example, color image data). Skeleton data (which consists of the approximate locations in space of joints, or of other ambiguous and/or diffuse anatomic structures) may in turn be calculated from the acquired depth and/or spectral data. Pixel label data (which consists of labeling pixels in acquired depth maps or color image maps, such that the labeled pixels correspond to the body surfaces of humans in the field-of-view) may also be calculated from the acquired depth and/or spectral data.

Any collection of distance measurements to (or between) objects in a field-of-view is referred to herein as "depth data". There are many ways to acquire, calculate, or otherwise generate depth data for a field-of-view.

For example, depth data may be calculated based on a "time-of-flight" method. In this method, light with known physical characteristics (such as wavelength) is emitted into a field-of-view. An energy sensor, such as a camera, receives the light that is reflected from the field-of-view. Changes in the physical characteristics of the light between its being emitted and its being received—for example, the round-trip transit time of a light pulse, or the phase shift of an emitted waveform—allow calculation of the distance to various objects (that reflect the light) in the field-of-view. If light pulses are utilized (for example, to measure round-trip transit time), the emitter can be, for example, a pulsed LED. If continuous light is utilized (for example, to measure phase shift), the emitter can be, for example, a laser. Time-of-flight cameras are a subset of LIDAR (Light Detection and Ranging) technologies, in which emitted-and-reflected light is used to remotely gauge the distance or other properties of a target. LIDAR cameras are similar to radar devices; the main difference is that radar bounces radio waves off target objects, but LIDAR uses ultraviolet, visible, or near-infrared light. Mesa Imaging AG, of Zurich, Switzerland, is an example of a company that manufactures devices to acquire depth data through time-of-flight: for example, its SR4000 time-of-flight camera.

Besides LIDAR, a different method of calculating depth data is through the use of "pattern deformation methods," also sometimes called "light coding". In pattern deformation methods, a light pattern with known physical characteristics (such as pattern shape and spacing) is emitted into a field-of-view. An energy sensor, such as a camera, receives the light pattern that is reflected from the field-of-view. Changes in the pattern between its being emitted and its being received—for example, gridlines moving closer further apart, or average distances between speckled dots growing or shrinking—allow calculation of the distance to various objects (that reflect the light) in the field-of-view.

In contrast to time-of-flight or LIDAR, the specific wavelengths or transit times of the emitted light are not crucial; what matters in pattern-deformation methods are the emitted pattern in which the light is placed, and how that emitted pattern is subsequently reflected and deformed by objects in the field-of-view. Because the specific wavelength is less important in pattern-deformation methods, a common choice of wavelength in such methods is infrared, which light cannot be seen by the human eye, and can be superimposed on a scene without disturbing people. If the light pattern is relatively fixed and constant, it is called "structured light"—often, structured-light patterns are grids of regular lines.

If the light pattern exhibits random or pseudorandom variation, it is called "coded light"—often, coded-light patterns are lattices of dots. (The reason why random or pseudorandom variations may be used in light patterns is so that small areas of the pattern will "look slightly different" compared to each other, enabling easier lining-up and registration of the emitted and reflected patterns.) PrimeSense Limited, of Tel Aviv, Israel, is an example of a company that manufactures sensors to acquire depth data through pattern deformation: its sensors are embedded in, for example, the Microsoft Kinect device (Microsoft Corp., Seattle, USA) and the Asus Xtion device (Asustek Computer Inc., Taipei, Taiwan).

Besides time-of-flight, LIDAR, and pattern deformation, a different method of acquiring depth data is through the use of emitted energy that is not light. For example, sound (rather than light) may be emitted and bounced off objects; the reflected physical characteristics of the sound, such as round-trip transit time, or frequency or phase shift, may be used to calculate depth or other characteristics of the objects in the field-of-view. Sommer Mess-Systemtechnik, of Koblach, Austria is an example of a company that manufactures devices to acquire depth data through ultrasonic impulses: for example, its USH-8 sensor, which uses ultrasonic impulses to measure snow depth.

Embodiments of the present invention may use any type of emitted and received energy, including but not limited to visible light, ultraviolet light, infrared light, radio waves, audible sound waves, ultrasonic frequencies, and pressure vibrations, in order to acquire depth data. Embodiments of the present invention are agnostic as to the source of depth data. As used herein, "depth data" refers to measurements of the distances to objects (or portions of objects) in a field-of-view.

Note that the term "camera" is used herein for convenience only, and any energy sensor, or image capture device, or energy capture device, or data capture device using various ranges of electromagnetic radiation or other types of energy may be used and substituted therefore. The terms "energy sensor", "camera," "image capture device," "energy capture device," and "data capture device" are used interchangeably herein. Some such devices need not emit electromagnetic radiation, because they capture energy based on reflected radiation already present in the environment. Other such devices may emit electromagnetic radiation and capture reflected radiation, such as ultrasonic transducers, and the like, where such emitted electromagnetic or other energy radiation is not present in the environment to a sufficient degree or sufficiently present in known directions relative to a target.

Additionally, the number of energy sensors are not limited to one or two such devices: one energy sensor, two energy sensors, or more than two energy sensors may be used (for example, to generate additional stereoscopic data, or to cover a larger region of space), as well as a single energy sensor.

"Image data" or "image" as used herein may refer to data or image captured by any of the above-mentioned devices or sensors, such as an energy sensor, a camera, an image capture device, an energy capture device, and/or a data capture device, and need not necessarily refer to the optical range. In one embodiment, image data may refer to the same visual-spectrum data that would be generated by a standard digital camera, consisting of a 2D photographic pixel map, where each pixel represents a visible color. Note that in general, "color" as used herein may refer to all the colors of the visual spectrum, or a grayscale spectrum, or any other palette of visual colors that are perceptible by the human eye. As used herein, "color image data" refers to visual (visible to the human eye) image data, similar to that captured by a standard consumer digital camera.

Figure 1B:
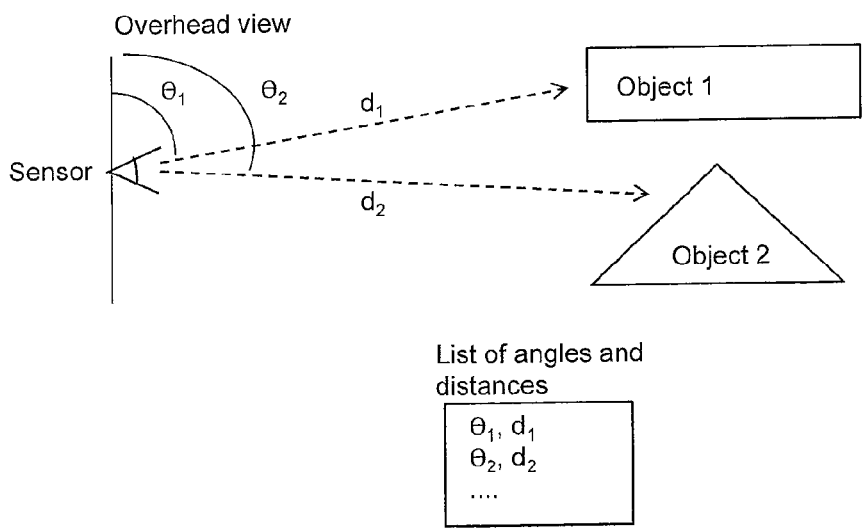

"Depth data" is less intuitive than color image data. Depth data represents the distance from a sensor to a nearest object in space. FIGS. 1A and 1B show two representations of depth data. The preferred representation of depth data, shown in FIG. 1A, is a 2D bitmap, also sometimes referred to as a depth map. However, alternate representations are also possible. The value of each (x, y) pixel in the 2D bitmap shown in FIG. 1A represents the distance from a common reference plane—typically a vertical plane established by the sensor itself, with the x-axis running horizontally, and the y-axis running vertically—to the closest physical object, along a normal ray projected outward from the common reference plane at that (x, y) coordinate. (In such a coordinate system, since the y-axis extends floor-to-ceiling, and the x-axis extends to left-and-right of the sensor, it follows that the z-axis extends straight out from the sensor into the field-of-view.)

A 2D depth data bitmap therefore corresponds to a quantized contour, or topographic, map of the sensor's field-of-view. Equivalently, a pixel value z at position (x, y) in the data bitmap indicates that the surface (or edge) of a real-world object exists at coordinate position (x, y, z) in physical space.

A depth bitmap can represent depth data only for aspects of an object that are visible to the sensor: any aspects of an object that are out-of-view of the viewpoint are "invisible" and not represented in the depth bitmap.

For example, if we were to obtain a depth data bitmap of the Moon as taken from standing on the Earth, we would find that a collection of pixels in the middle of the bitmap formed the shape of a circle. The pixels in the center would have the lowest distance values (they would correspond to the central part of the Moon which is closest to the Earth), and the pixels at the edge of the circle would have the highest distance values (they would correspond to the edge of the visible face of the Moon). Pixels outside the circle of the Moon, representing the void of space, would have maximum distance values (essentially equivalent to infinity). The "dark side of the Moon", invisible to us, would not be represented in the bitmap at all.

FIG. 1B shows an alternate representation of depth data, in which the positions of objects in the field-of-view are described using a list of angles and distances. Such a representation is not as advantageous as the bitmap approach, due to the complexity of "working backwards" to identify which objects are placed where in space.

Figure 2A:
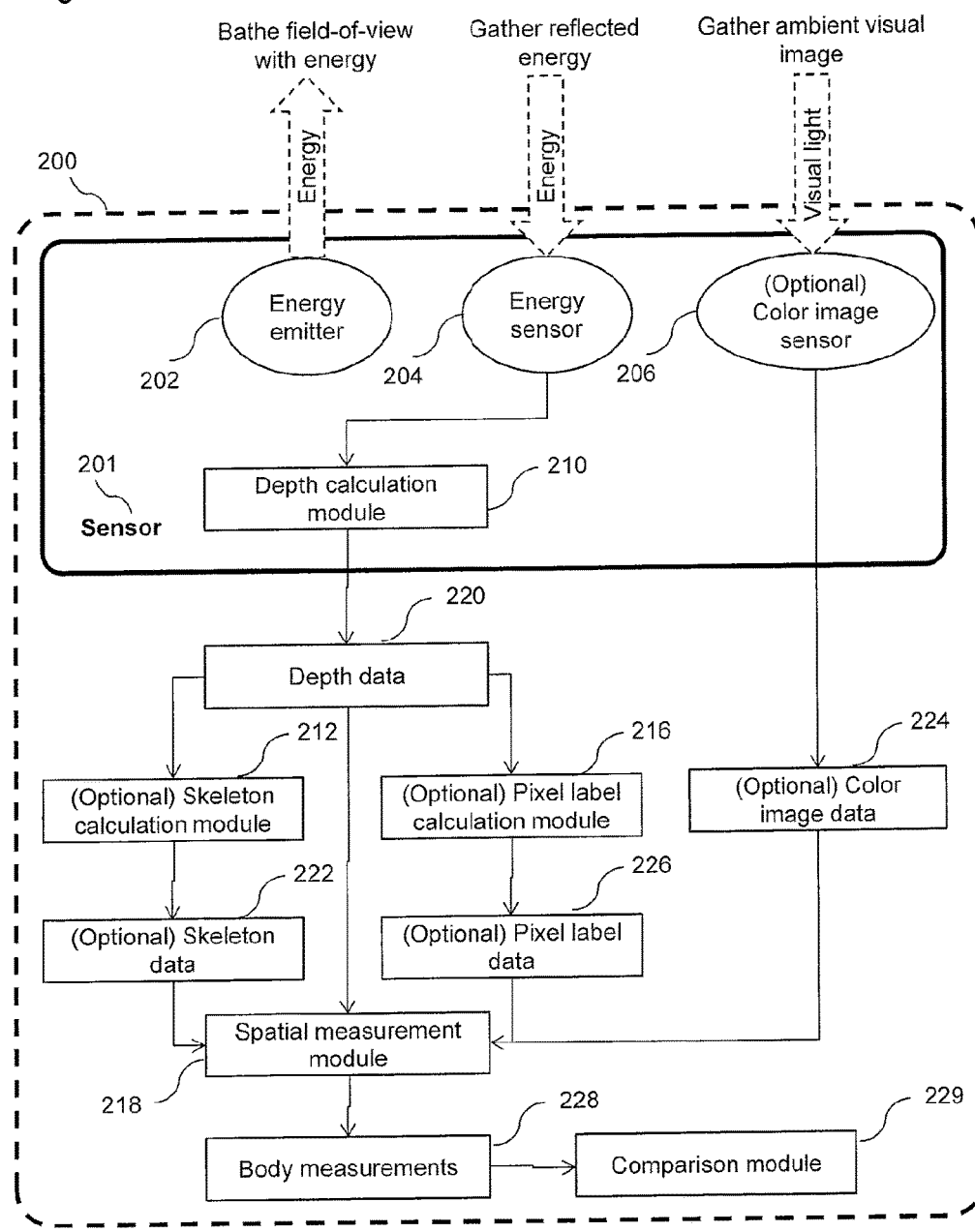

FIG. 2A shows a block diagram of an embodiment of the present method and system. A system for detecting deterioration of health status (the system) is shown generally as 200, which may be used to carry out the method disclosed in this document. As set forth above, any form of active energy capture (emission of energy and capture of the reflected energy) or passive energy capture (capture of reflected energy based on ambient energy sources) may be used.

As shown in FIG. 2A, energy emitter 202 bathes the field-of-view with energy. As described previously, the energy emitted may comprise visible light, or non-visible light, or sound, or any other type of energy. The energy emitted may bathe the entire field-of-view all at once, or may bathe different parts of the field-in-view in turn. Energy sensor 204 gathers the energy that is reflected or received from objects in the field-of-view. Depth calculation module 210 calculates the distances to objects in the field-of-view using the information acquired by energy sensor 204. As described previously, such depth calculation may performed using time-of-flight, or LIDAR, or pattern deformation, or any other method suitable for calculating depth measurements. Depth calculation module supplies depth data 220, where, for example, depth data 220 may be structured in a form similar to that shown in FIG. 1A.

In FIG. 2A, depth calculation module 210 uses the captured energy data from energy sensor 204 to calculate depth data 220 corresponding to the objects in the field-of-view. Such calculation may also rely on knowledge of the characteristics of the most recent energy characteristics or energy patterns emitted by energy emitter 202, and/or on past energy characteristics or energy patterns emitted by energy emitter 202, or captured by energy sensor 204, or on any other information required to carry out depth calculations.

Sensor portion 201 encapsulates a minimal set of components required by some embodiments of the present inventive method, viz., an energy emitter, an energy sensor, and a depth calculation module. Because of the similarity to energy sensor 204, optional color image sensor 206 is included for convenience within sensor portion 201. It is important to note that sensor portion 201 is a label of convenience, roughly corresponding to the typical hardware components required for some real-world embodiments of the present inventive method, and so any components of the present inventive method, including all of those, for example, shown in FIG. 2A, may be brought in or out of sensor portion 201. For example, optional skeleton calculation module 212 could appear inside sensor portion 201 in some embodiments of the present inventive method.

The depth data 220 may be used by optional skeleton calculation module 212 in order to construct optional skeleton data 222, consisting of a set of approximate spatial locations of anatomic joints (e.g., the [x, y, z] locations of shoulder, hip, and ankle). The data from depth calculation module 220 may also be used by optional pixel label calculation module 216 in order construct optional so-called "pixel label" data 226, consisting of labeling individual pixels in a depth map (such as the depth map shown in FIG. 1A) that correspond to a human being in the field-of-view. A wide variety of machine learning methods are known in the art that may be utilized by optional skeleton calculation module 212 and optional pixel label calculation module 216, and are not discussed further here.

Spatial measurement module 218 uses depth data 220 to calculate measurements in space, as described further below. Spatial measurement module 218 supplies body measurements 228. For example, a body measurement 228 might be the distance between the heel of one foot, and the heel of the other foot. Comparison module 229 uses body measurements 228 to determine baseline measurements for an individual, and to compare subsequent measurements in order to detect a deterioration in health, as described further below. Comparison module 229 may use any suitable methods, such as statistical methods, cluster methods, neural networks, and the like, to determine baseline measurements and deviations thereof. A wide variety of methods to detect deviations from baseline are known in the art, including standard deviation calculations, chi-squared tests, t-tests, Bayesian networks, and many others.

It is possible to calculate body measurements using only depth data 220; however, the accuracy of the depth pattern, or of body measurement calculations derived from depth data alone, may be insufficient, and it may also be difficult to clearly delineate separate objects using depth data alone. Therefore, in some applications it may be preferable to also include a standard color image sensor 206, which gathers visual data in the same way as a standard digital camera. Optional color image sensor 206 supplies optional color image data 224.

For example, if two objects in the field-of-view are close together, such that the energy received received by energy sensor 204 does not lead to clearly distinguishable depth data 220, their different visual colors received by the color image sensor 206 may be used to help distinguish the objects from each other. However, for many applications of system 200, the color image sensor 206 and the color image data 224 are optional.

As noted above, it is possible to calculate body measurements using only depth data 220. However, the speed of body measurement calculation may be improved by drawing upon additional calculations performed on depth data 220.

For example, optional skeleton data 222 may be calculated from depth data 220, and used to improve the speed of calculating body measurements 228. For example, optional pixel label data 226 may be calculated from depth data 220, and used to improve the speed of calculating body measurements 228. As described previously, optional skeleton data 222 describes the approximate spatial locations of anatomic joints (for example, the three-dimensional [x, y, z] locations of shoulder, hip, and ankle). As described previously, optional pixel label data 226 distinguishes which pixels in a depth map (if any) correspond to a human being, and which do not.

In FIG. 2A, the depth data 220 consists of a set of calculated depth data, where such data may conform, for example, to the representation shown in FIG. 1A. The optional color image data 224 consists of a set of image data; such data may, for example, be represented in the same way as images that are acquired by a typical, everyday consumer digital camera, such as by using a pixel array or raster. The optional skeleton data 222 consists of a set of calculated spatial measurements of the approximate locations of portions of a user's body, for example, shoulders and knees; such data may, for example, be represented by a set of (x,y,z) coordinates. The optional pixel label data 226 consists of a set of pixel labels delineating which pixels correspond to a human being in the field-of-view; such data may, for example, be represented by a pixel array or raster.

Embodiments of the system 200 preferably utilize a combination of depth data 220, optional color image data 224, optional skeleton data 222, and optional pixel label data 226, to conduct measurements of an individual's body surface. The system 200 can utilize depth data 220 alone, at the potential cost of decreased accuracy and/or speed.

The sensor portion 201 of FIG. 2A may alternately utilize more than two image sensors. For example, the sensor portion 201 of FIG. 2A may be augmented with a third image sensor (not shown), which may overlap in energy type or frequency with either the energy sensor 204 or the optional color image sensor 206, in order to provide an additional nearby stereoscopic vantage point by which to increase accuracy of depth calculations. Or, multiple sensor portions 201 may be combined—for example, by placing a different sensor portion 201 in each room of a house, then combining together their collective data to cover a larger area than a single sensor portion 201 is capable of covering.

FIG. 2B shows another embodiment of the present inventive method. FIG. 2B is similar to FIG. 2A, except that optional pixel label calculation module 216 and optional pixel label data 226 of FIG. 2A are omitted, to emphasize that they are not required for some embodiments. All items in FIG. 2B correspond to their like-numbered items in FIG. 2A.

FIG. 2C shows another embodiment of the present inventive method. FIG. 2C is similar to FIG. 2A, except that optional color image sensor 206 and optional color image data 224 of FIG. 2A are omitted, to emphasize that they are not required for some embodiments of the present inventive method. All items in FIG. 2C correspond to their like-numbered items in FIG. 2A.

FIG. 2D shows another embodiment of the present inventive method. FIG. 2D is similar to FIG. 2A, except that optional pixel label calculation module 216 and optional pixel label data 226 and optional color image sensor 206 and optional color image data 224 of FIG. 2A are omitted, to emphasize that they are not required for some embodiments of the present inventive method. All items in FIG. 2D correspond to their like-numbered items in FIG. 2A.

FIG. 2E shows another embodiment of the present inventive method. FIG. 2E is similar to FIG. 2A, except that optional skeleton calculation module 212 and optional skeleton data 222 and optional pixel label calculation module 216 and optional pixel label data 226 and optional color image sensor 206 and optional color image data 224 of FIG. 2A are omitted, to emphasize that they are not required for some embodiments of the present inventive method. All items in FIG. 2E correspond to their like-numbered items in FIG. 2A.

FIG. 2F shows another embodiment 270 of the present inventive method. FIG. 2F shows an example of the present inventive method that uses pattern-deformation and infrared (IR) light to acquire depth measurements. In FIG. 2F, IR pattern emitter 272 is analogous to energy emitter 202 of FIG. 2A. In FIG. 2F, IR pattern sensor 274 is analogous to energy sensor 204 of FIG. 2A. In FIG. 2F, optional color image sensor 276 is analogous to optional color image sensor 206 of FIG. 2A. In FIG. 2F, depth calculation module 280, optional skeleton calculation module 282, depth data 290, optional skeleton data 292, and optional color image data 294, are analogous to their counterparts (respectively) 210, 212, 220, 222, 224 of FIG. 2A.

In FIG. 2F, optional pattern pre-processing module 275 may clean, sharpen, remove noise from, or otherwise modify the information from IR pattern sensor 274. In FIG. 2F, optional color image pre-processing module 277 may clean, sharpen, remove noise from, or otherwise modify the information from optional color image sensor 276. Referring again to FIG. 2A, energy sensor 204 may optionally be accompanied by a pre-processing module (not shown) analogous to optional pattern pre-processing module 275. Referring again to FIG. 2A, optional color image sensor 206 may optionally be accompanied by a pre-processing module (not shown) analogous to optional color image pre-processing module 277. Alternatively, in FIG. 2A, any pre-processing—if needed—analogous to components 275 and 277 of FIG. 2F may be incorporated within (respectively) energy sensor 204 and optional color image sensor 206.

In FIG. 2F, depth calculation module 280 draws on the information transmitted by optional pattern pre-processing module 275—or directly on IR pattern sensor 274, if 275 is not present—and may optionally also draw on the information transmitted by optional color image pre-processing module 277—or optionally directly on optional color image sensor 276, if 277 is not present—in order to calculate depth data 290. The color image itself, if present, may also be maintained separately as optional color image data 294. The depth data calculation module 280 does not require any information from color image pre-processing module 277 or optional color image sensor 276, but may optionally utilize such information to improve the accuracy of depth data 290.

The data from any combination of IR pattern sensor 274, optional pattern pre-processing module 275, optional color image sensor 276, optional color image pre-processing module 277, and depth calculation module 280, may be used by optional skeleton calculation module 282 in order to construct optional skeleton data 292, consisting of (as described previously) a set of approximate spatial locations of anatomic joints (for example, the [x, y, z] locations of shoulder, hip, and ankle). Similar to the depth calculation module 280, the skeleton calculation module 282 requires only information from IR pattern sensor 274 and/or optional pattern pre-processing module 275, and preferably information from depth calculation module 280.

Although not shown in FIG. 2F, components analogous to optional pixel label calculation module 216 and optional pixel label data 226 of FIG. 2A may be placed in an analogous relationship in FIG. 2F as their counterparts in FIG. 2A. For example, an optional pixel label calculation module in FIG. 2F (not shown) could receive the same inputs as optional skeleton calculation module 282, and produce optional pixel label data (not shown), as described previously. For brevity, FIG. 2F does not display such analogs to optional pixel label calculation module 216 and optional pixel label data 226 of FIG. 2A.

Once the input data for body measurements (depth data 290, optional skeleton data 292, optional color image data 294, and/or optional pixel label data [not shown]) are obtained, the system 200 may utilize a computer 298, including a processor 295, RAM 296, and ROM 297, to execute a series of operations on the input data in order to produce measurements of the user's body surface, as described further below. Alternatively, such processing may be performed by dedicated hardware chips and circuits, each of which may have their own internal processor.

The resulting body surface measurements may be placed into a data storage device 284, shown on a display device 285, and/or transmitted over a communication interface 286, such as the Internet. The system may be operated by the user through user input 287; such input may include hand gestures, voice commands, keyboard, mouse, joystick, game controller, or any other type of user input.

In some embodiments of system 270, the depth calculation module 280 is a component of (or calculated by) computer 298, rather than sensor portion 271. In some embodiments of system 270, the optional skeleton calculation module 282 is a component of (or calculated by) computer 298, rather than sensor portion 271. In some embodiments of system 270, the optional pixel label calculation module (not shown) is a component of (or calculated by) computer 298, rather than sensor portion 271. In general, depth data 290, optional skeleton data 292, and optional pixel label data (not shown) may be generated by modules at various points within system 270, so that their generation is not limited to sensor portion 271.

Because system 200 and system 270 perform similar functions, and share similar inputs and outputs, we will use "system 200" herein to refer interchangeably to both of system 200 and system 270, unless otherwise noted. Similarly, and for the same reasons, sensor portion 201 and sensor portion 271; energy emitter 202 and analogous IR light emitter 272; energy sensor 204 and analogous IR pattern sensor 274; optional color image sensor 206 and 276; depth calculation module 210 and 280; optional skeleton calculation module 212 and 282; depth data 220 and 290; optional skeleton data 222 and 292; optional color image data 224 and 294; will each be referred to interchangeably, unless otherwise noted.

The system 200 (or 270) may measure the user extremely quickly, and with minimal requirements to pose or position the body. In particular, for an individual measurement of the user, the system 200 requires only a single data-snapshot of the user. Thus, in some embodiments, the user may need to stand relatively still for only a predetermined amount of time, for example 0.001 second to 0.1 second, which in an optical camera, may be determined by the amount of lighting, shutter speed, and aperture size. Other types of image capture or energy capture devices may operate on a much faster basis so that such capture is substantially instantaneous, at least from the perspective of the user.

In other embodiments, the user need not necessarily stand in one position or maintain a particular position for any amount of time, and may be able to move in real-time within the field of view of the image capture device. Individual measurements from different data-snapshots may also be combined or operated upon further, for example by adding them or averaging them, as described below.

The term "data-snapshot" or "snapshot", as used herein, refers to a single set of depth, and/or image, and/or skeleton data, and/or pixel label data, wherein the data are gathered substantially simultaneously with each other. As noted previously, a single data-snapshot cannot account for any "invisible" or "dark side" aspects of objects in the field-of-view. Where necessary to complete a measurement, therefore, the system 200 "fills in" for invisible aspects by using heuristics that may take advantage of the symmetry of the human body—for example, by doubling a visible half-circumference to estimate the full circumference of a limb. This process is described in further detail below.

The original construction of optional skeleton data 222 may utilize multiple calculations on depth and/or image data over time. The system 200 is agnostic as to the means by which optional skeleton data 222 are generated. From the point of view of the system 200, a single—substantially instantaneous—data-snapshot of depth, and/or image, and/or skeleton data, and/or pixel label data, is sufficient to obtain a particular body surface measurement, regardless of the prior post-processing that was necessary to generate the content of that data-snapshot.

Similarly, the original construction of depth data may utilize multiple calculations on data received from either energy sensor 204 or optional color image sensor 206 individually, or from both energy and color image sensors 204 and 206 collectively over time. For example, a particular image received at one moment in time by either energy sensor 204 or optional color image sensor 206 may serve as a so-called reference image at a subsequent moment in time, such that two or more images taken slightly apart in time are used to calculate depth data. Again, the system 200 is agnostic as to the means by which depth data, including depth data 220, are generated, including image processing that may occur over time, or different physical methods such as time-of-flight, LIDAR, or pattern deformation.

Through the use of a substantially instantaneous snapshot of data, gathered from one or more stationary cameras, the system 200 avoids the use of body-worn devices such as accelerometers, or the wearing of special clothing. As is described further below, this method also avoids the need for manual intervention—in particular, the need for a second person to conduct body measurements. Some embodiments of the system 200 may be thought of as draping "virtual health status updates" in three-dimensional space on top of different parts of the user's body, simultaneously and almost instantly, acting as a sort of "virtual health monitor."

In some embodiments of system 200, energy sensor 204 and optional color image sensor 206 may be placed near each other, as a substantially co-located array, rather than being physically dispersed throughout different points on the perimeter of a field-of-view. Such co-location is ideally as close as possible in order to have the field-of-view be similar for each sensor. The feasible co-location separation distance depends upon the size of the physical components. For example, if energy sensor 204 and optional color image sensor 206 are instantiated as CMOS chips, the chips and their supporting electronics and optics may be placed such that their borders are, for example, approximately 5 mm apart, and the centers of their lenses are, for example, approximately 2 cm apart.

In general, the co-located sensors are preferably positioned with a separation distance of millimeters to centimeters, although smaller and larger distances are possible. Similarly, the angles of view of the co-located sensors are preferably within a few degrees of each other. This means that embodiments of the present system and method may be very compact and portable, e.g., fitting easily on a shelf or at the base of a television at home.

Figure 3A:
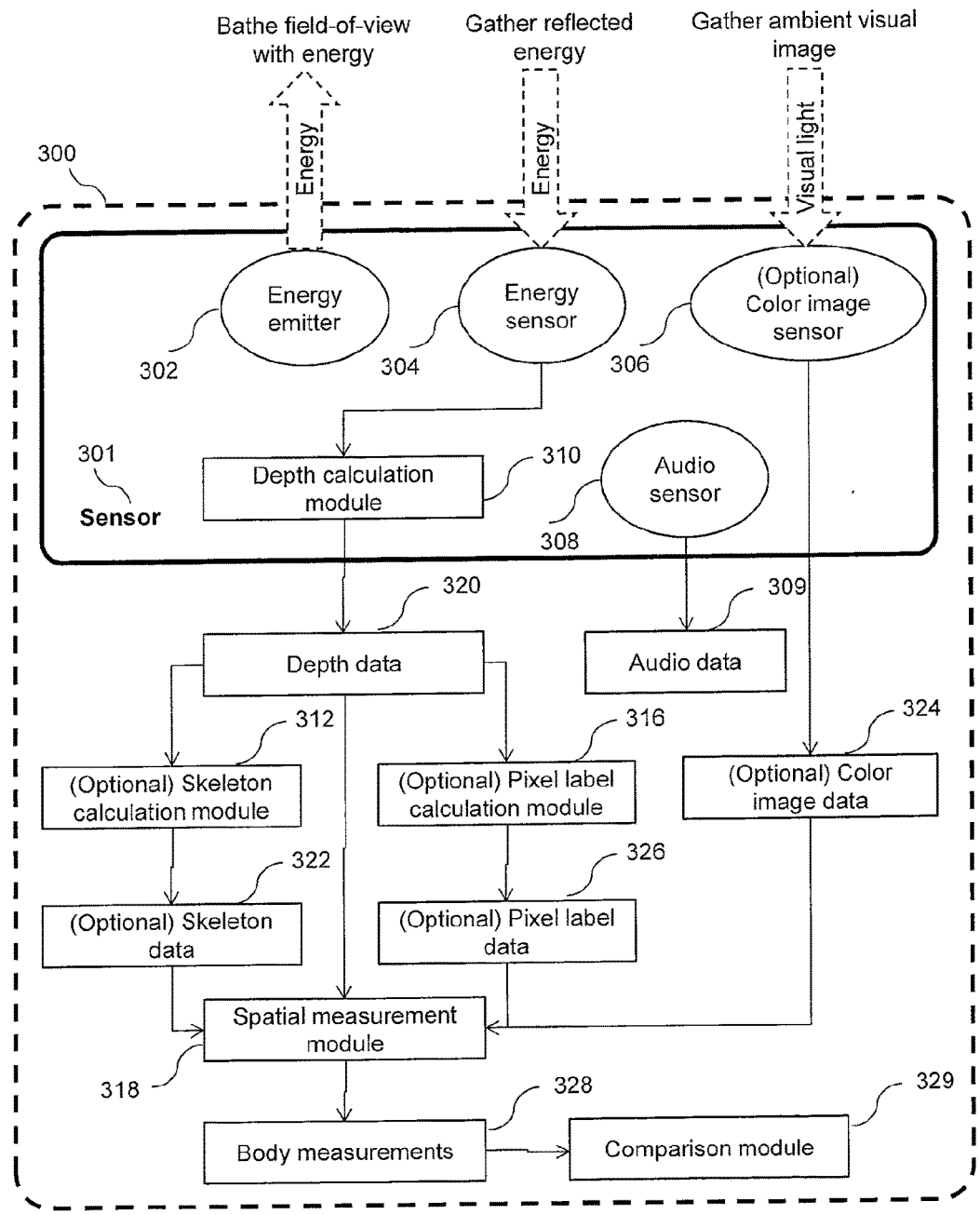
FIGS. 3A and 3B show additional block diagrams according to specific embodiments of the present system and method.

FIG. 3A shows another block diagram of an embodiment of the present system and method. A system for detecting deterioration of health status (the system) is shown generally as 300, which may be used to carry out the method described in this document. As compared to FIG. 2A, FIG. 3A demonstrates the addition of a sensor to detect audio (sound) in the environment, in particular, the sound of the user's speech. In FIG. 3, items 300 to 329, with the exception of 308 and 309, are equivalent to their like-numbered items in FIG. 2A. Audio sensor 308 captures ambient audio, for example, through the use of a microphone or microphone array, and outputs audio data 309. Audio data 309 may be represented in any way appropriate for conveying sound or an audio signal, for example, as an analog waveform, or as a digital mp3 data file.

Figure 3B:
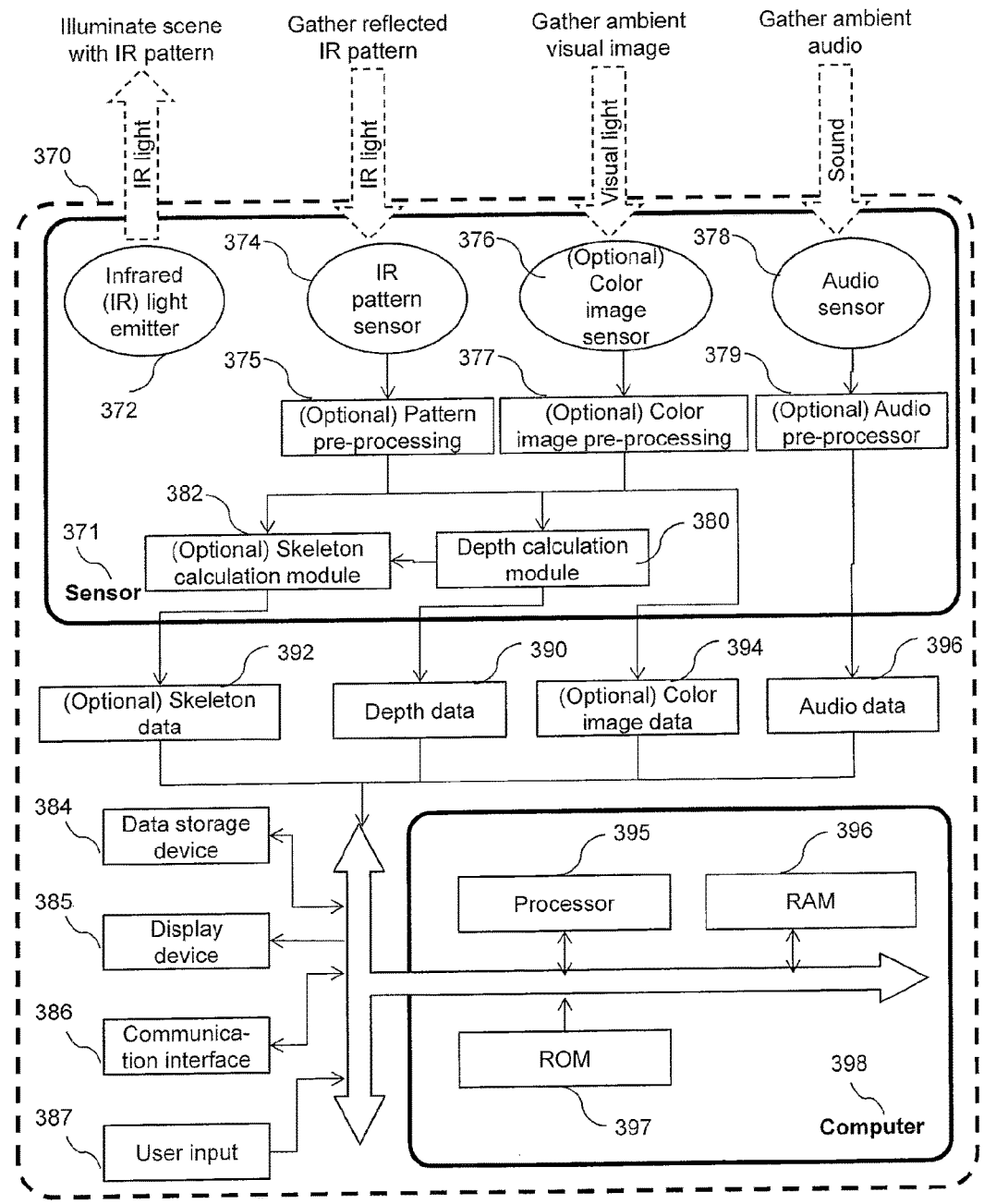

FIG. 3B shows another block diagram of an embodiment of the present system and method. A system for detecting deterioration of health status (the system) is shown generally as 370, which may be used to carry out the method described in this document. As compared to FIG. 2F, FIG. 3B demonstrates the addition of a sensor to detect audio (sound) in the environment, in particular, the sound of the user's speech. In FIG. 3B, items 370 to 398, with the exception of 378, 379, and 396, are equivalent to their like-numbered items in FIG. 2F. Audio sensor 378 captures ambient audio, for example, through the use of a microphone or microphone array. Optional audio preprocessor 379 carries out any desired preprocessing on the data received from audio sensor 378. An example of preprocessing would be identifying the physical location in space, relative to the audio sensor 378, from which the sound emanated, by comparing two audio data streams (stereo signal) against each other. The output audio data 396 conveys any desired combination of raw and preprocessed audio data to other parts of the system 370, including the computer 398. Audio data 396 may be represented in any way appropriate for conveying sound or an audio signal, for example, as an analog waveform, or as a digital mp3 data file.

System 300 (or system 370), as a superset of system 200, can by definition do everything that system 200 (or system 270) can do. For reasons of brevity and simplicity, this document will often refer to "system 200" instead of "system 200 and/or system 270 and/or system 300 and/or system 370", but it should be understood that "system 300" (or "system 370") can always be substituted in place of "system 200" (or "system 270"). The converse is not true, because system 300 (or system 370) possesses audio capabilities that system 200 (or system 270) does not possess.

Depth calculation module 210, optional skeleton calculation module 212, optional pixel label calculation module 216, spatial measurement module 218, comparison module 229, and all other modules described herein, may be implemented in circuitry as a physical component or processing element, whether integrated or discrete, or may be implemented to the extent possible, in software to be executed by the processor or specialized processing circuitry.

For a single measurement, certain embodiments of the system 200 may require only a single data-snapshot of the user, taken from a single point of view. This is because the system 200 may use heuristics—such as the inherent symmetry of the human body—to "fill in", or compensate for, any invisible depth or image information that is invisible to the sensor portion 201. Furthermore, multiple measurements may be drawn from a single snapshot.

However, for a measurement of a body portion to be taken, that body portion should be substantially in view of the sensor portion 201. As a general rule, about half of the body portion is preferably visible to the sensor in order for that body portion to be measured (because symmetry or heuristics can be used to deduce the shape of the other half).

For example, to measure the volume of the abdomen, the user typically substantially faces the sensor; if the user presents a back profile (equivalent to a back view) to the sensor portion 201, then the front of the user is invisible altogether, and the abdominal volume cannot be measured. Conversely, to measure the volume of the seat, a side or back profile of the user may be required, because the seat is invisible from a front view. Similarly, to measure the length or width of a foot, either the foot must be profiled so that the sole of the foot is facing the sensor, allowing both measurements to be conducted from the same data-snapshot; or else the length must be measured on its own from a side profile (of the foot), and the width measured separately using a front or back profile (of the foot).

Another reason that multiple data snapshots may be required is due to noise in the system. If the inputs or outputs at any component of sensor portion 201 are noisy—that is, varying randomly or non-randomly, due either to inherent aspects of sensor portion 201 or to external environmental conditions, then multiple data snapshots may be required to extract improved signal from the noisy background. For example, data snapshots may be averaged over time, using signal processing methods, in order to have noise "cancel out" and thereby diminish over time, while constructively adding together (strengthening) the valuable signal. If such averaging over time is performed, then multiple data snapshots may be required for higher-accuracy measurements.

Another reason that multiple data snapshots may be required is to track a change in measurement over time. For example, the calculation of walking speed over time requires corresponding multiple data snapshots over time. In some embodiments of the system 200, to track measurements that change over time, measurements will be acquired at a sampling rate ranging from approximately 30 data snapshots per second, to approximately 1 data snapshot per 30 seconds. The duration of time during which measurements are tracked may be predetermined. For example, in some embodiments of the system 200, measurements will be carried out on an ongoing basis, indefinitely (e.g., until the user chooses to stop the system 200 from running). In other embodiments of the system 200, measurements will be carried out only during certain time intervals (e.g., only during daytime).

Therefore, although any one measurement may require only a single snapshot, nonetheless, in some embodiments, more than one snapshot may be used to obtain a complete set of desired measurements, or to track how measurements change over time.

There are three primary profiles, or views, that the user may present to the sensor portion 201:
1) Front profile: the user directly faces the sensor.
2) Side profile: the user stands at a ninety-degree angle to the sensor, presenting either the left or right side.
3) Back profile: the user stands facing directly away from the sensor.

Many additional profiles, besides the three listed above, are possible—for example, facing the sensor obliquely, that is, at an angle—and so the list of profiles above is not intended to be exhaustive. Additional profiles are within the scope of the system 200. For example, a different set of poses may be preferable for disabled persons (e.g., a set of profiles in which the person would sit instead of stand). For example, in measuring the amount of time over the day that a user sits down versus stands up, a preferred profile may consist of the user being in a seated position.

The relationship of direct body measurements to the three primary profiles is shown in FIG. 4. As used herein, a "direct" body measurement is a measurement taken directly on the user's body (or of the user's voice). As used herein, a "derivative" body measurement is a measurement that is calculated from one or more other measurements (which may each be either direct or derivative). For each measurement shown in FIG. 4, the "preferred profile" is the first-choice profile of the user with which to conduct that measurement, and the "alternate profile" is a backup choice that may be used in place of (or in addition to) the preferred profile.

Figure 5:
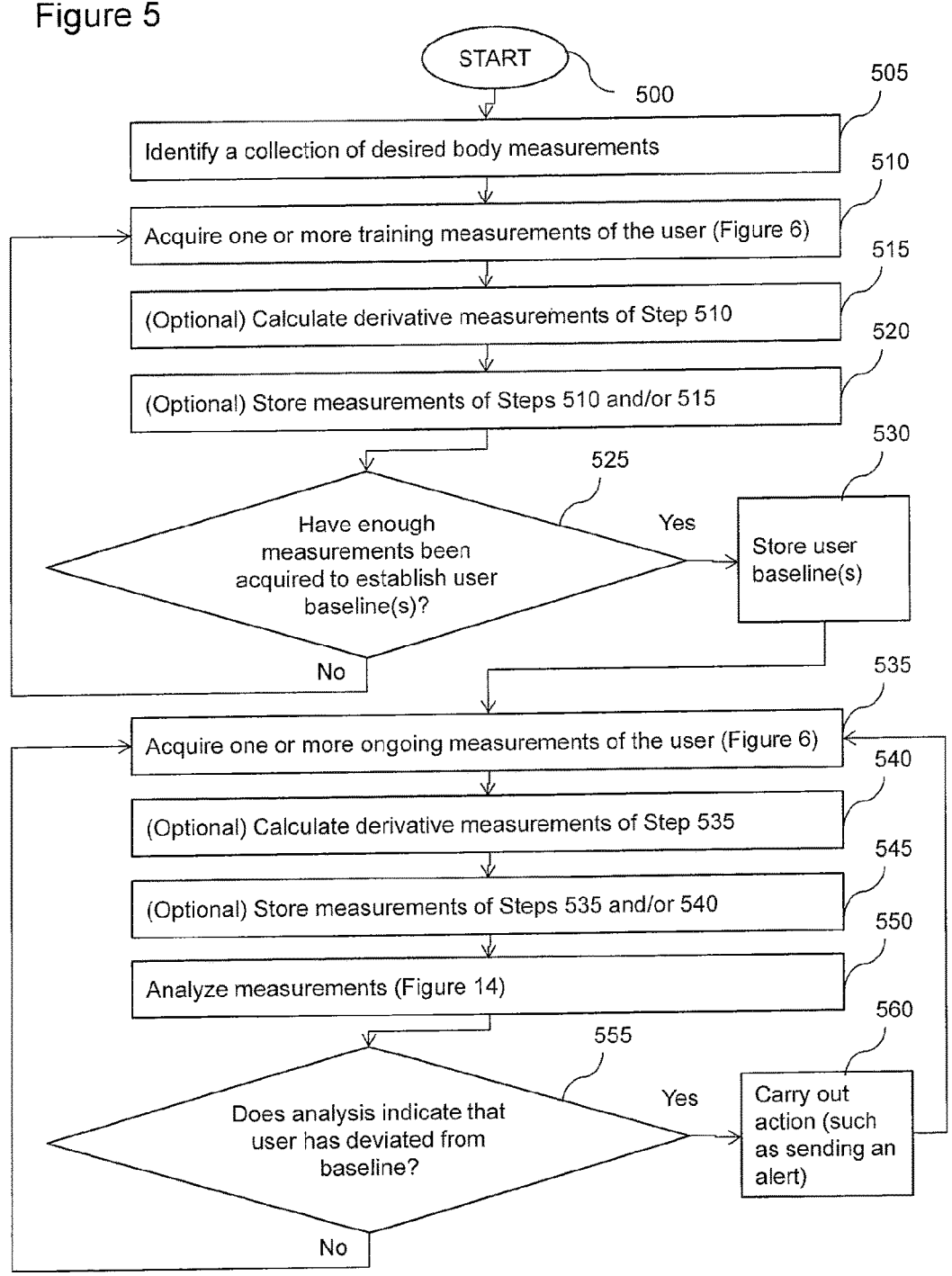
FIG. 5 shows a high-level flowchart according to a specific embodiment of the present method.

FIG. 5 shows a high-level flowchart describing a preferred embodiment of the present inventive method, beginning at step 500. In Step 505, a collection of body measurements is identified. For example, Step 505 might include the collection of measurements relevant to the gait of an individual, such as stride length, or knee-to-knee distance. In Step 510, a set of measurements are acquired. (Which specific measurements are collected at any moment in time may be opportunistic, because the types of measurements that can be collected will depend on which profile the user presents to the sensor portion 201 at that particular moment in time, as described further in FIG. 6). In Step 515, any desired "derivative measurements" are calculated. A "derivative measurement" is a measurement that is not acquired directly from the user, but that is calculated based on other measurements. For example, the angle of the lower limb, relative to vertical, is a direct measurement, acquired by analyzing the current positioning of the parts of the user's body; while the acceleration, or rate of change, of that angle is an indirect (derivative) measurement, that is calculated over time. It is apparent from this example that derivative measurements may incorporate a component of time. In Step 520, the measurements of Steps 510 and/or 515 may be stored.

In Step 525, the collected measurements over time are evaluated to determine whether a user baseline may be established. By "baseline," we mean a typical range of measurements for the user, in the user's current state of health. When enough data has been acquired to establish a baseline, then the baseline data may be stored in Step 530. For example, Step 530 might contain the typical ranges of user activity (e.g., stride length, time spent walking each day, arm range of motion at the shoulder) when the user is in a state of normal health.

Step 535 marks the advent of "ongoing" measurements, as opposed to the "training" measurements of Steps 510-525. In Step 535, similar to Step 510, a set of measurements is opportunistically acquired. Step 540 calculates any desired derivative measurements, and Step 545 may store the measurements.

Figure 14:
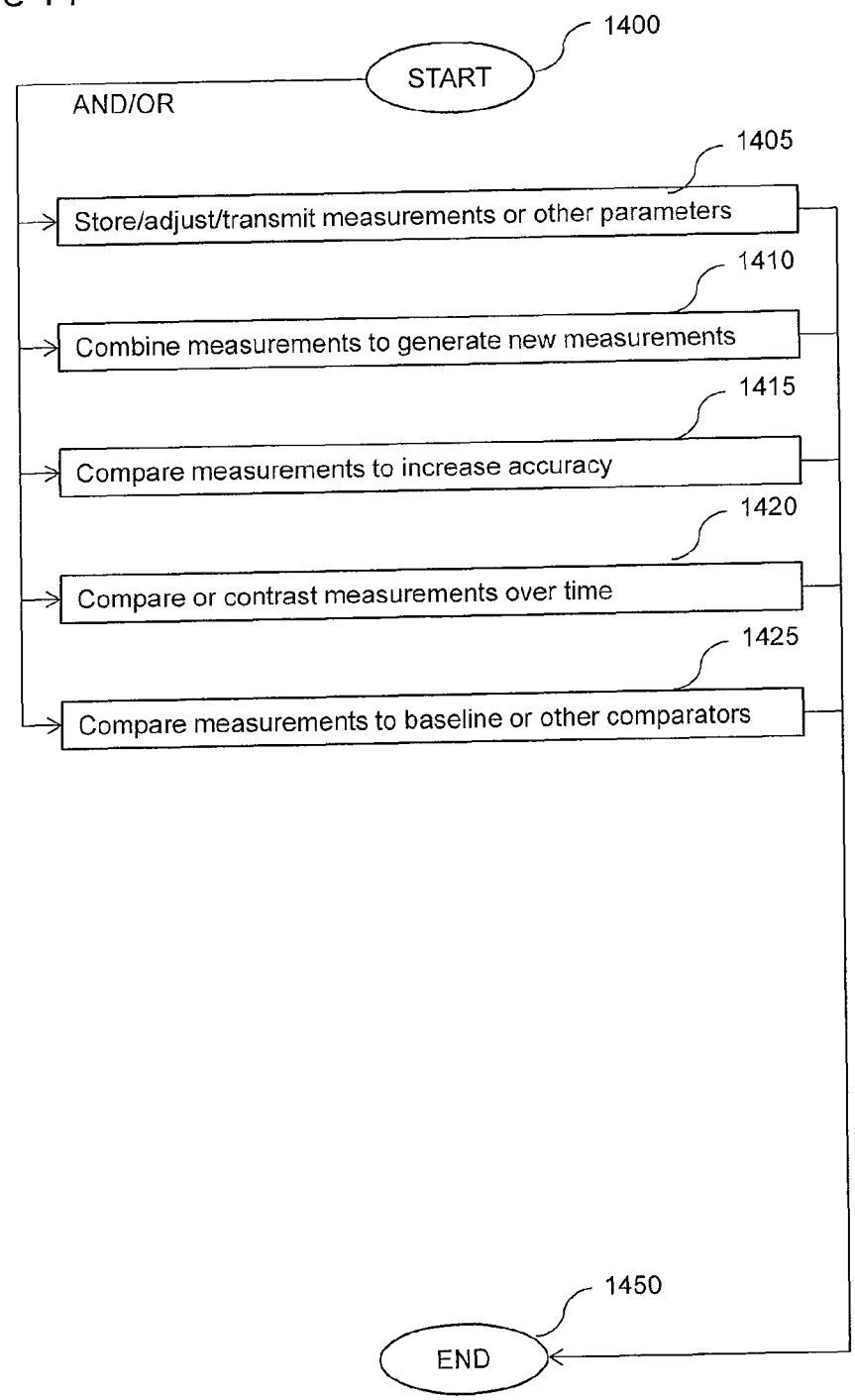
FIG. 14 shows several actions that may be undertaken once a collection of measurements has been completed.

In Step 550, additional actions may be undertaken on the measurements acquired so far, as described further in FIG. 14. In particular, the measurements of Steps 540 and 545 may be compared to the baseline measurements of Step 530. Step 555 evaluates the results of Step 550 to decide whether the user's ongoing set of measurements deviate significantly from the baseline of Step 530. This may be done, for example, through simple methods such as thresholds, or through more complex methods such as statistical analysis, or via any method that enables comparison of training and ongoing measurements. Step 560 is triggered if a significant deviation from baseline is detected; it carries out an action relevant to the deviation, for example, sending an alert of the deviation to another system or to a the user or another human being. For example, Step 560 might send an alert as a text message to a designated mobile phone, or as a clinical alert to an electronic medical record.

As described above, if the system is noisy, then system 200 may acquire multiple data snapshots in order to better extract signal from the noisy background. In such cases, any of Steps 510, 515, 535, or 540 may check whether all desired measurements have been acquired according to a desired accuracy or threshold. An example of an accuracy might be, continue acquiring and averaging data snapshots until a pre-specified standard deviation of the data value is achieved. An example of a threshold might be, acquiring 60 data snapshots, at a rate of 30 data snapshots per second, and averaging depth map data values across them. Another example of a threshold might be, that the user views the results of the data measurement and process and decides whether to continue acquiring additional measurements or not. In general, Steps 510, 515, 535, and 540 allow any type of calculation or decision-making process to improve signal extraction from noise.

In general, it is possible for the system to respond, in real-time, to the user's posture and profile, and opportunistically acquire measurements as the user moves around, in any order of measurements. Another embodiment of system 200, further demonstrating such real-time interactivity, is described further below and displayed in FIG. 15.

As set forth in FIG. 5 and, more generally in other embodiments, it is possible to perform measurements of not just the user's body surface, but of garments that the user is wearing—for example, if such garments are obscuring or covering a portion of the user's body surface. So, in general, the steps in FIG. 5 may apply to either the user's body surface, or to garments that the user is wearing at the time of measurement.

Throughout this document, for purposes of brevity and clarity, we will refer to measurements of the user's body surface; but it should be understood that measurements of garments worn by the user also fall, in all respects, within the scope of the system and method, and that all discussions and figures herein pertain both to the measurement of a user's body as well as to measurement of any garments that may be worn by the user at the time of measurement.

Figure 6:
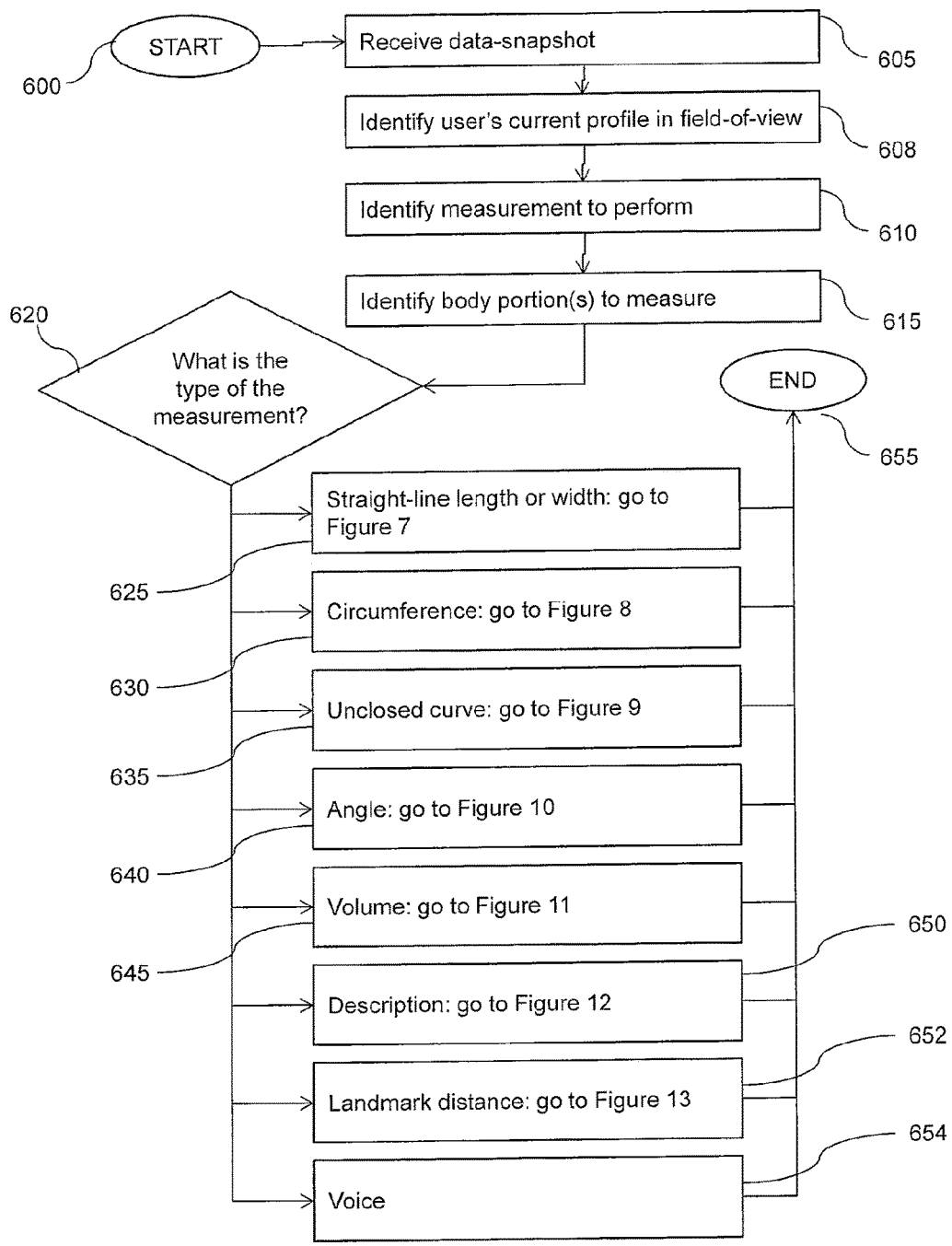
FIG. 6 shows a flowchart to obtain a single measurement according to a specific embodiment of the present method.

FIG. 6 is a flowchart showing the steps that are undertaken to carry out an individual measurement, beginning at Step 600. (It follows that Steps 510 and 535 each invoke the steps of FIG. 6 for each individual measurement that needs to be conducted.) FIG. 6 shows Steps 605, 608, 610, and 615 to, respectively, receive a data-snapshot, identify the user's current profile in that data-snapshot (e.g., front view, side view), identify a particular measurement to perform on that snapshot, and identify which body portion is most relevant to that measurement. For example, Step 605 might receive a data-snapshot; Step 608 might determine that the data-snapshot contains a front-profile of the user, for example, by looking for the presence of two eyes, or by measuring the depth distance from sensor portion 201 to each shoulder; Step 610 might identify that a knee-to-knee distance is the next measurement to be performed; and Step 615 might identify that the two upper legs are the most relevant body portions to measure for that measurement.

Step 610 might be implemented using a queue data structure that is created and initially populated in Step 505. Step 615 might be implemented using a lookup table similar to FIG. 4, but with columns that are body portions (e.g., upper arm, torso, head) rather than user profiles.

There are seven primary types of body surface measurements:

Straight-line length or width: the linear distance between two points

Circumference: the distance of a closed loop (possibly non-circular) around a portion of the body Unclosed curve: the distance along an arbitrary unclosed curve in space that follows the surface of the body Angle: the distance either between two body portions, or between a body portion and a coordinate axis Volume: the volume of a body portion Description: a qualitative description of a body portion, as follows:
- a. Stance (forward-backward): e.g., normal, forward-leaning, backward-leaning, erect
- b. Stance (side-side): e.g., normal, left-leaning, right-leaning, erect
- c. Shoulder slope: e.g., normal, steep, flat
- d. Male chest: e.g., thin, fit, normal, muscular, large
- e. Abdomen (a.k.a. stomach): e.g., thin, normal, medium, large
- f. Seat: e.g., thin, normal, curved, large The seventh primary type of body surface measurement is "landmark distance", which means, the straight-line distance between any two distinguishing landmarks on the body surface. For example, step length might be calculated from the "landmark distance" between the tip of the left and right feet.

An additional measurement—though not of the body surface—as shown in Step 654, is a measurement of the user's voice, such as timbre, volume, or cadence.

It should be appreciated that the lists of measurements and of qualitative descriptions shown above are not exhaustive, and that the scope of embodiments of the present system and method is not limited to these specific measurements and qualitative descriptions; additional types of body surface, ambient environment, or voice measurements may be identified and carried out by the system.

Embodiments of the present inventive method may use the identification of landmarks on the human body in order to conduct body measurements. A "landmark" as used herein is any point, or border, or in general, any distinguishing location or set of locations, on the body surface, or on worn garments, that may be identified and tracked in three-dimensional space with accuracy sufficient for the body-sizing application at hand. Examples of landmarks might include the spatial position of the head of the ulna of the right arm, or the tip of the big toe of the left foot. For analyzing gait, an example of a typical required accuracy might be approximately 1-2 centimeters; so that, for example, a gait application might identify and track the 3D spatial location of the tip of the big toe of the left foot (among other measurements) within approximately 1-2 centimeter accuracy in real-time.

Landmarks are distinguished from the skeleton data 222 by the precision, reproducibility, and reliability of landmarks. Skeleton data 222, if present, generally consist of approximate locations of nebulously defined portions of the body, or collections of anatomic structures. Skeleton data can be thought of as guideposts to general regions of the human body. Most often, they correspond to joints of the human skeleton, such as the shoulder or knee, because machine recognition algorithms may be employed to recognize structures that stay relatively constant in shape while moving, such as arms and legs, and therefore these algorithms may also be used to identify the approximate articulation regions between, say, arms and legs.

An example of skeleton data would be the approximate 3D spatial location of the right shoulder joint. The right shoulder joint is of nebulous definition both structurally and spatially; it consists of multiple anatomic components (portions of the arm, ribcage, surrounding musculature, and so forth) and cannot be precisely located on the human body, only approximately outlined. The skeleton data corresponding to the right shoulder joint, therefore, cannot be used to precisely locate and track (over time) a specific portion of the shoulder, because these skeleton data do not refer to any particular part of the shoulder joint.

Furthermore, skeleton data may be erratic or "jitter" over time, depending on the underlying machine recognition algorithms being employed, again because they don't refer to any specific, particular location in space. Skeleton data are therefore, in general, incapable of being used to conduct precise measurements.

Landmarks are further distinguished from the pixel label data 226 by the precision, reproducibility, and reliability of landmarks. Pixel label data 226, if present, consist of labels that may be applied to individual pixels in depth data 220, or to individual pixels in optional color image data 224. The use of these labels, when they are present, is to distinguish human beings from each other, and from the ambient environment, in a field-of-view.

For example, if depth data 220 were represented by a 640 by 480 pixel depth map of a field-of-view, and if the depth pixel at coordinate (400, 200) corresponded to a distance to a portion of the body surface of a human being; the depth pixel at coordinate (500, 300) corresponded to a distance to a portion of the body surface of a different human being; and the depth pixel at coordinate (20, 50) corresponded to a distance to a door or a wall in the local environment, then depth pixel (400, 200) might be labeled "person #1", depth pixel (500, 300) might be labeled "person #2", and depth pixel (20, 50) might be labeled "non-person".

Similar reasoning applies to optional color image data 224. In sum, if depth data 220 or optional color image data 224 are represented as pixels—for example, in an array or raster representation—such pixels may be attached with labels that distinguish whether the pixel corresponds to a person or a non-person, and if a person, an arbitrary identifier for the person, where such labels are maintained in system 200 as optional pixel label data 226.

As with optional skeleton data 222, the optional pixel label data 226 generally cannot be used to precisely locate and track (over time) a specific portion of the human body. Optional pixel label data 226 are generally able to signify, for example, that a specific pixel in a particular data snapshot belongs to a surface of a human body and not the ambient environment; or that two different pixels belong to two different human bodies.

Optional pixel label data 266 generally cannot uniquely identify a person's identity (for example, they cannot label that a person is "John H. Watson who lives at 221B Baker Street", as opposed to "person #1"), nor can optional pixel label data 226 generally label a portion of a body (for example, they cannot label that a pixel belongs to "person #1's right shoulder" as opposed to just "person #1"). Optional pixel label data 266 are therefore equivalent to a type of "mask", as the term is known in computer science—applying this pixel label "mask" to depth data 220 or to optional color image data 224 highlights which pixels, if any, correspond to an arbitrarily numbered human being.

Furthermore, similar to optional skeleton data 222, optional pixel label data 226 may be erratic or "jump" over time, depending on the underlying machine recognition algorithms being employed or on the noise of the overall system 200. Pixel label data are therefore, in general, incapable of being used to conduct precise measurements.

A wide variety of methods to calculate skeleton data and/or pixel label data as outputs, using depth data and/or color image data as inputs, are known in the art, and may draw upon machine learning, statistical, or other technologies or methods. For example, the Microsoft Kinect For Windows Software Development Kit (SDK), from Microsoft Corp. of Seattle, USA, provides software routines to calculate skeleton data and pixel label data (called "player identification" in the Kinect for Windows SDK) from depth data and/or color image data.

For example, the OpenNI open-source software framework, under the auspices of the OpenNI Organization, similarly provides software routines to calculate skeleton data (called "joint data" in OpenNI) and pixel label data (called "figure identification" in OpenNI) from depth data and/or color image data. The Kinect for Windows SDK and the OpenNI framework employ different computational methods, utilize different APIs, have different operating characteristics, and represent information differently. They are mentioned here as illustrations of potential methods to calculate skeleton data 222 or pixel label data 226. The system 200 is agnostic as to the means by which skeleton data 222 or pixel label data 226 are generated. In distinction, "landmarks" as used herein are, by definition, of sufficient accuracy to conduct body measurements suitable for the particular application at hand, including real-time applications such as gait analysis. The word "terminus", as used herein, is a special case of "landmark": a terminus is a landmark that is a single point on the surface of the body (as distinguished from, for example, a border or a curve or a set of locations).

Note that some embodiments of the present inventive method use types of energy, such as infrared light from IR light emitter 272, that cannot penetrate worn garments. Other embodiments may employ energy patterns that are able to penetrate worn garments. However, because such penetrating radiation may be harmful to human health, or may pose privacy hazards, some embodiments preferably rely on emitted energy of types, such as infrared, that do not penetrate worn garments. For many applications, such as gait analysis, it is important to be able to measure either the surface of the human body directly, or of interposed worn garments that closely approximate the surface of the human body. As a result, some embodiments may place constraints on the nature of the clothing worn during execution of a particular application. For example, an application to track smoothness of arm motion for a Parkinson's Disease patient may require the user to wear a relatively tight-fitting shirt, rather than, say, a billowy parka.

In the descriptions and Figures that follow, it should be appreciated that often only depth data are required to carry out body measurements. For example, depth data alone—or, optionally, a combination of depth data, and the skeleton data that are calculated from the depth data—may be sufficient to carry out a measurement of stride length, because such data may enable identification of all necessary body landmarks (e.g., points on the foot and ankle) and measure distances between those landmarks. In other cases, depth data are preferably combined with color image data, or a combination of depth data, calculated skeleton data, calculated pixel label data, and color image data may be preferable. In general, identifying the position of a body landmark requires utilizing some combination of depth data 220, optional skeleton data 222, optional pixel label data 226, and optional color image data 224, but the specific combination, and the specific requisite calculations carried out on that combination, differ from landmark to landmark.

Steps 625 through 652 of FIG. 6 refer to additional Figures, respectively, to pursue each specific type of measurement to conduct.

Figure 7:
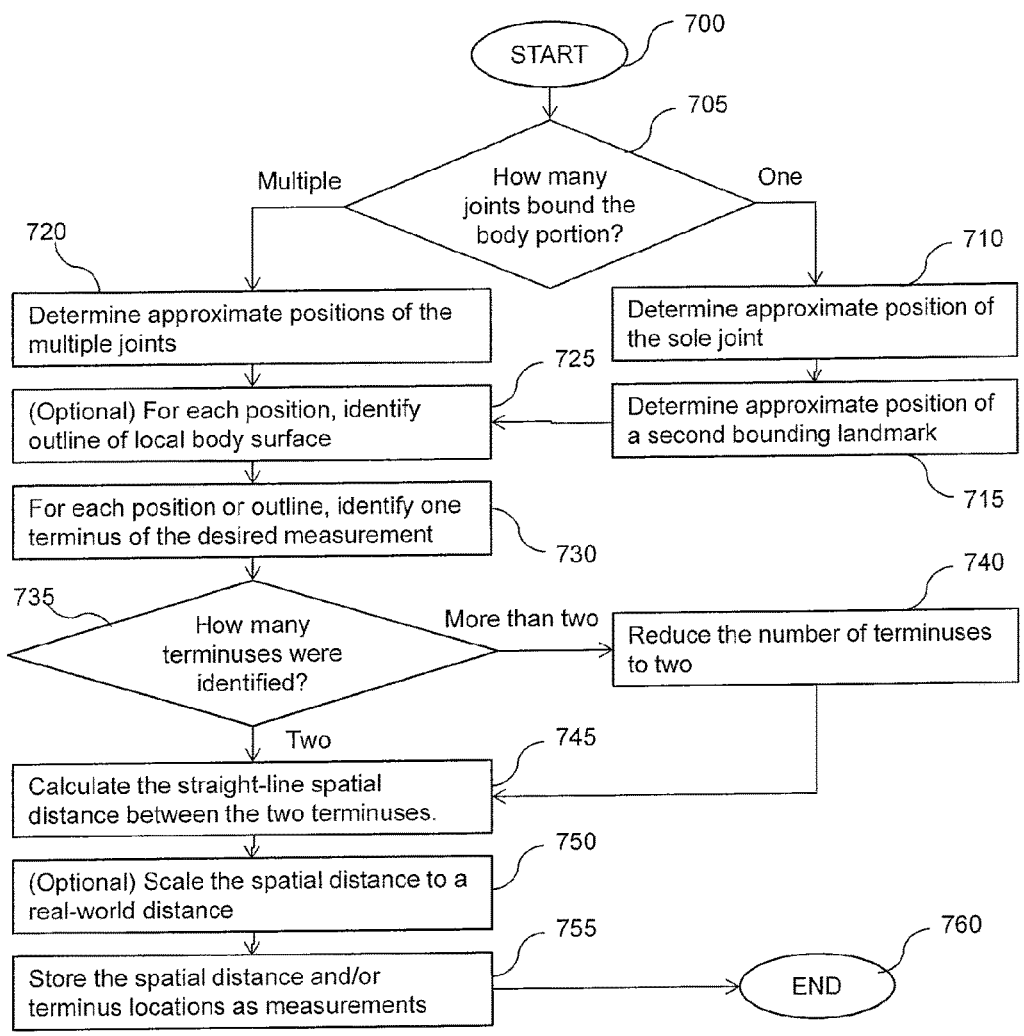
FIG. 7 shows a flowchart to obtain a straight-line length or width measurement according to a specific embodiment of the present method.

FIG. 7 is a flowchart showing the execution of a straight-line length or width measurement beginning at Step 700. (It is assumed in FIG. 7, without loss of generality, that only one body portion was identified in Step 615; distances across multiple body portions can be calculated through adding together individual measurements.) Step 705 evaluates the body portion that was determined in Step 615 of FIG. 6. For example, this body portion might be the head or an upper-arm. Step 705 counts the number of joints that bound the body portion; this may be easily done using a simple lookup table. If there is only one bounding joint (for example, the only bounding joint for the head is the neck), then Step 710 determines the approximate (x, y, z) position of this sole joint. The preferred way to determine this position is to perform a lookup in the optional skeleton data 222 supplied by the sensor portion 201. If skeleton data are not available, then image-segmentation methods may be used to identify the approximate location of the bounding joint. In Step 715, a second bounding landmark is determined. For example, an appropriate second bounding landmark for the head is the very top of the head. The position of this bounding landmark is determined, as before, using skeleton data or image-segmentation methods.

Step 705 may alternately determine that multiple joints bound the body portion that was determined in Step 615 of FIG. 6. For example, the upper arm is bounded by shoulder and elbow joints (two joints in total); and the torso is bounded by two shoulder joints and two hip joints (four joints in total). Step 720 determines the approximate position of each joint, again using either skeleton data or image-segmentation methods.

In Step 725, the local body-surface outline, or silhouette, is determined around each joint or landmark position. For example, if a position corresponds to the elbow, then the local silhouette of the elbow is determined. The silhouette may be determined from a combination of depth data and/or color image data and/or pixel label data, using image-segmentation methods. The silhouette may be determined from depth data alone; in some cases, this may result in a degradation of accuracy (for example, if two body portions overlap too closely). The preferred representation of each outline generated by Step 725 is as a "mask" or labeling of pixels that is superimposed on the color image data 224 and depth data 220. Each outline thus describes a set of (x, y, z) locations of pixels that correspond to the body surface local to each joint or landmark position.

In Step 730, each outline from Step 725 is assigned a single terminus. The word "terminus", as used herein, refers to a single point that corresponds to a location on the surface of the user's body; a terminus may be represented, for example, as an (x, y) pixel location in a depth or image bitmap, or as an (x, y, z) point in space. The assignation of a terminus may be done using heuristic or computational methods. For example, the terminus of an elbow outline might be the point on the elbow midline that is furthest away from the ground in a front profile (in which profile the arm is extended to the side, as described previously).

As another example, the terminus of the top of the head might be the point on the surface of the head that is most distant from the ground. Step 735 invokes Step 740 if more than two terminuses were identified. Step 740 reduces the number of terminuses to exactly two, using heuristic or computational methods. For example, if the height of the torso is being measured, then the two shoulder terminuses might be collapsed to a single terminus halfway between them, and similarly for the two hip terminuses, thus reducing the original four terminuses to just two terminuses.

In Step 745, the straight-line spatial distance between the two terminuses of Step 735 or 740 is calculated. In Step 750, this straight-line spatial distance is optionally scaled to a real-world distance (as opposed to distance in pixels). In Step 755, the straight-line spatial distance measurement and/or terminus locations may be stored for further use, and the routine exits at Step 760.

Figure 8:
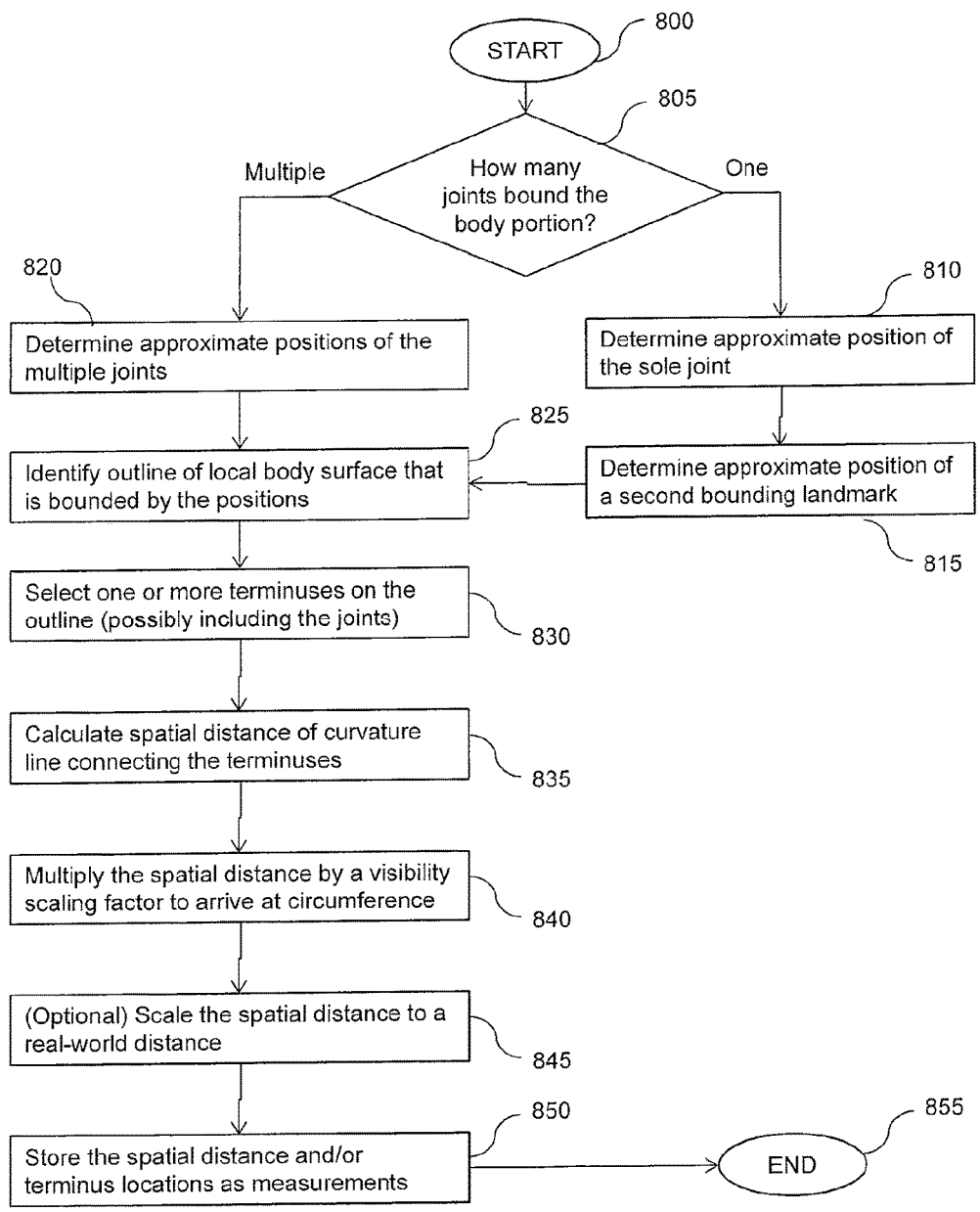
FIG. 8 shows a flowchart to obtain a circumference measurement according to a specific embodiment of the present method.

FIG. 8 is a flowchart showing the execution of a circumference measurement, beginning at Step 800. The word "circumference" as used herein refers to the distance along a closed loop in space (which may or may not be circular). Steps 805 through 820 are equivalent to their like-numbered steps 705 through 720, described previously. Step 825 determines the body-surface outline, or silhouette, of the body portion bounded collectively by the joint or landmark positions from Steps 820 or 810 through 815. For example, if the shoulder and elbow are the two bounding positions, then Step 825 determines the outline of the body portion that is the upper arm, as bounded by the shoulder and elbow.

This determination of Step 825 is performed in a similar fashion to Step 725, described previously; however, 825 determines the outline of a single body portion that is bounded by joint or landmark positions, rather than, as in 725, the outline of separate areas that are each local to a joint or landmark. This determination 825 provides an incomplete representation of the surface of the body portion in question, because approximately half of the body portion is invisible to the sensor at any one time; for example, only half of the upper arm is visible to the sensor at any one time.

Step 830 may use heuristic or computational methods to assign one or more (x, y, z) terminuses to the outline of the body portion identified in 825. For example, if the upper arm is the body portion of interest, one terminus might be assigned to the point on the outline most distant from the ground (corresponding to the top of the thickest point of the biceps muscle), and the other terminus assigned to the point on the outline directly opposite (corresponding to the bottom of the arm directly below the thickest part of the biceps muscle). Another way to assign terminuses would be to select periodically-spaced points along the path of steepest curvature following the body portion surface.

Step 835 calculates the distance of the curvature, tracking the surface of the user's body, that connects together the terminuses of Step 830. An arbitrary number of terminuses may be so connected, in order to better approximate the real-world distance along the surface of the body portion of interest.

Step 840 multiplies the distance that was calculated in Step 835 by a so-called "visibility scaling factor". This factor compensates for the "invisible" aspect of the body portion. Because a body portion will typically be half-visible to the sensor, this factor is preferably simply the number 2 (reflecting the approximate symmetry of the human body). The result of Step 840 is a full circumference value.

Step 845 optionally scales the circumference value from Step 840 to a real-world distance, as described previously. In Step 850, the circumference measurement and/or terminus locations may be stored for further use, and the routine exits at Step 855.

Figure 9:
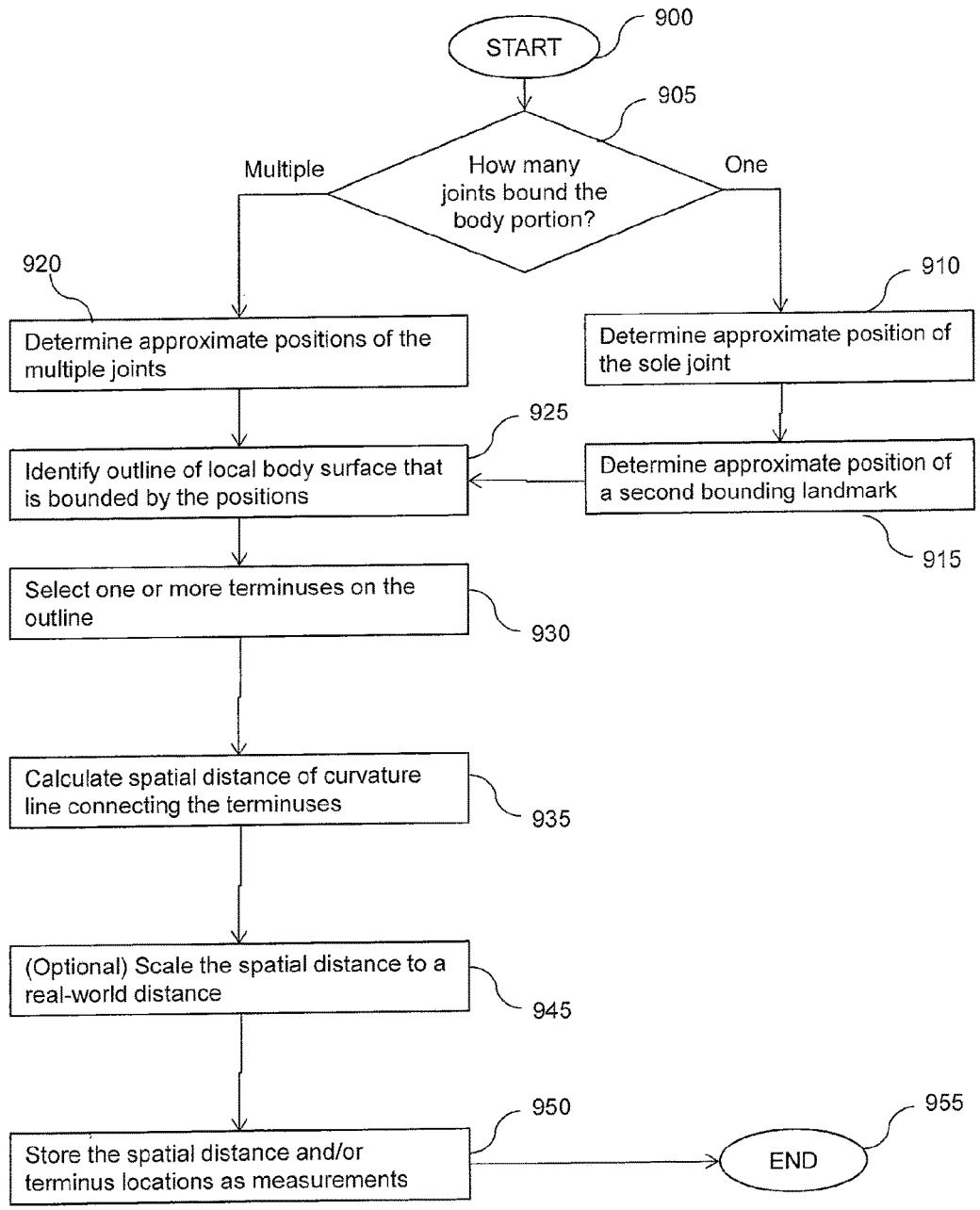
FIG. 9 shows a flowchart to obtain a length of an unclosed curve measurement according to a specific embodiment of the present method.

FIG. 9 is a flowchart showing the execution of a distance measurement along an unclosed curve that tracks the body surface, beginning at Step 900. This flowchart is equivalent to FIG. 8, except that the analog of Step 840 of FIG. 8 (multiplying by a visibility scaling factor) is omitted in FIG. 9. This is because, unlike a circumference, it is difficult to estimate the "invisible" aspect of an arbitrary unclosed curve using symmetry or other heuristics.

Figure 10:
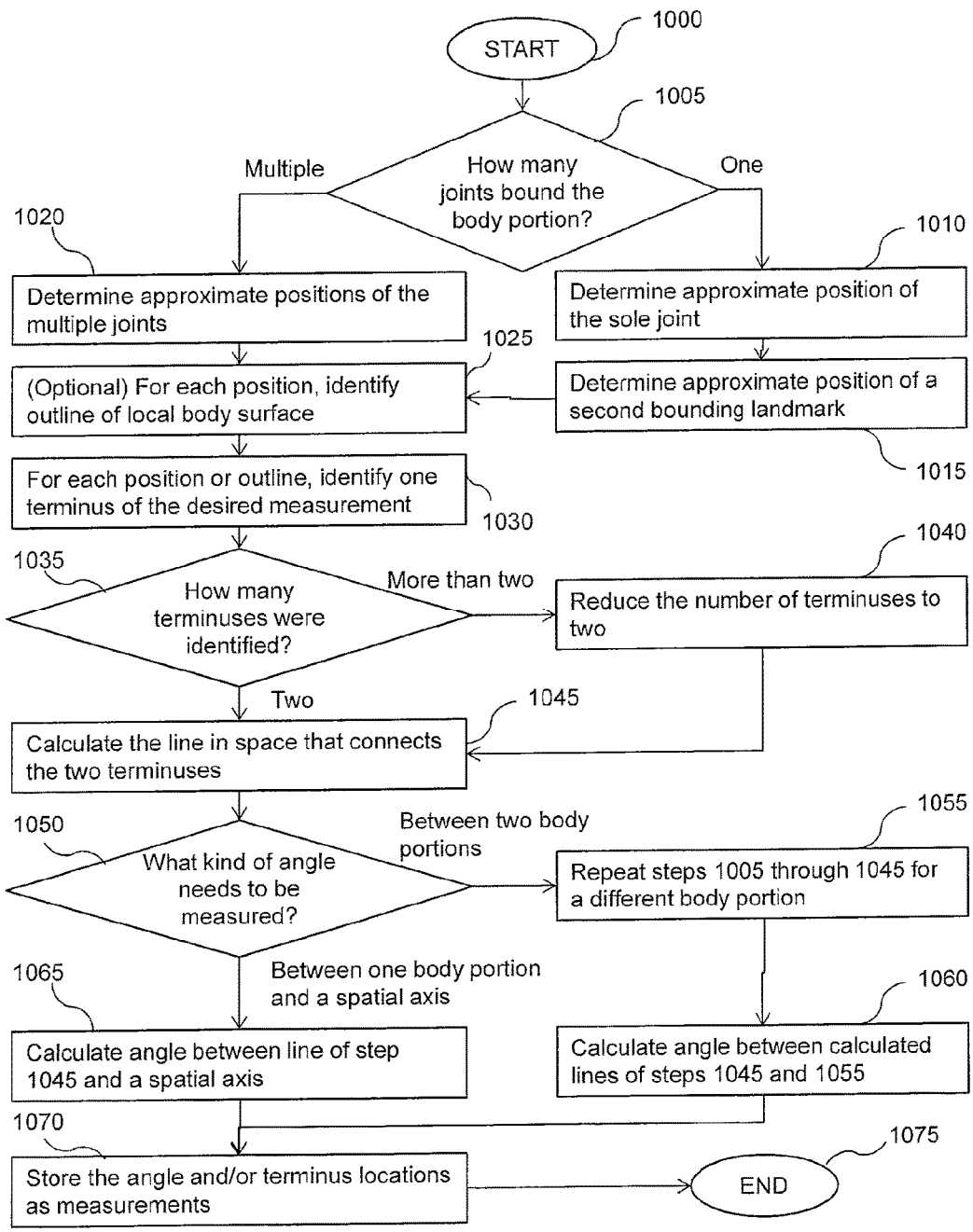
FIG. 10 shows a flowchart to obtain an angle measurement according to a specific embodiment of the present method.

FIG. 10 is a flowchart showing the execution of an angle measurement, beginning at Step 1000. Steps 1005 through 1040 are the same as their like-numbered steps 705 through 740 in FIG. 7. In Step 1045, though, rather than calculate the distance along a line connecting two terminuses as in Step 745, the equation of the line itself is calculated. Step 1050 then decides between two types of angle calculations.

If an angle compared to a spatial axis (x, y, or z) is desired, then Step 1065 calculates the angle between the line equation of Step 1045 and the appropriate spatial axis. If an angle compared to another body portion is desired (for example, the angle between upper arm and lower arm at the point of the elbow), then Step 1055 repeats Steps 1005 through 1045 to arrive at second line equation (corresponding to the second body portion of interest), and Step 1060 calculates the resultant angle between the two computed line equations. Step 1070 may store the angle measurement and/or terminus locations for future use, and the routine exits at Step 1075

Figure 11:
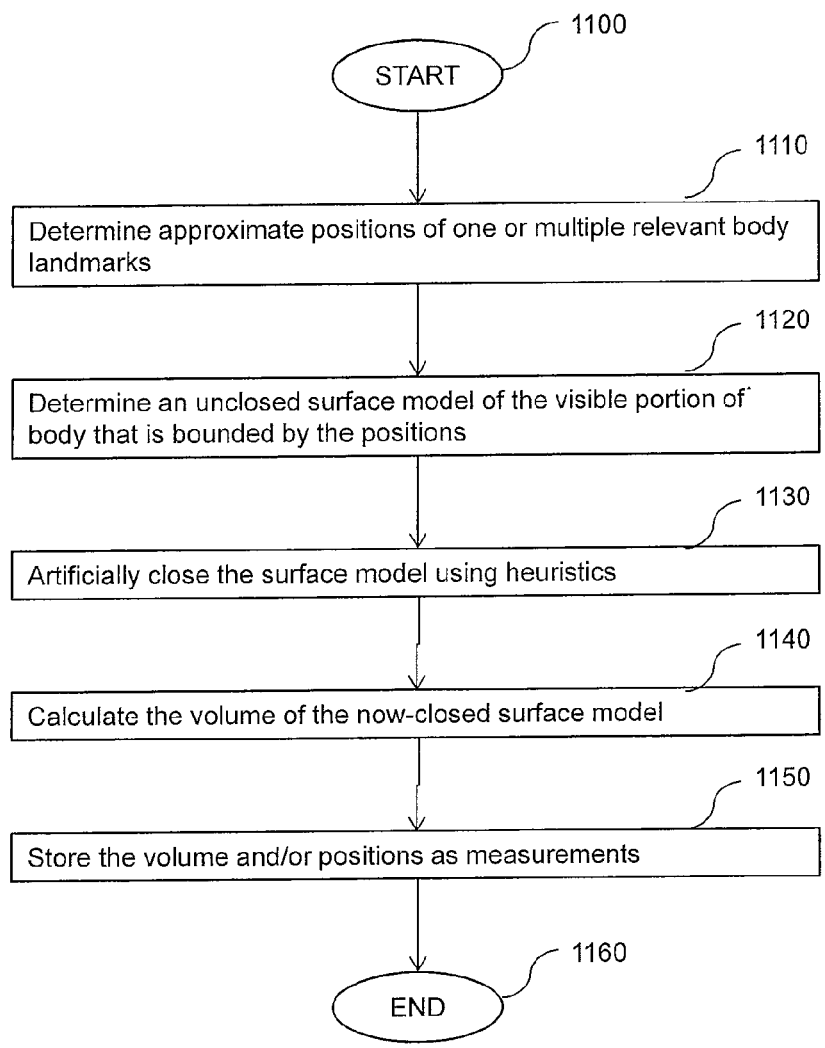
FIG. 11 shows a flowchart to obtain a volume measurement according to a specific embodiment of the present method.

FIG. 11 is a flowchart showing the execution of a volume measurement, beginning at Step 1100. In Step 1110, the positions of relevant body landmarks may be estimated. For example, landmarks for the abdomen might include the trough between the upper abdomen and the lower thorax, as well as the hips, and the approximate positions in space of those landmarks could be established using, for example, skeleton data or image segmentation methods. Step 1120 uses a data-snapshot to construct an unclosed (that is, incomplete or partial) surface model of the visible portion of the body that is bounded by the positions of Step 1110.

The surface model is necessarily unclosed and incomplete because, as described previously, aspects of the body portion will always be invisible to the sensor portion 201. For example, if the abdomen is viewed from the front, then the back part of the abdomen will be hidden from view of the sensor portion 201. Step 1130 artificially closes, or completes, the surface model using heuristics or approximations, such as symmetry. For example, if the volume of the abdomen is being measured from the front profile, leaving a "hole" in the back of the surface model where the abdomen is invisible to sensor portion 201, then Step 1130 might close the 3D model under the modeling assumption that the back wall of the abdomen is a flat vertical plate.

Step 1140 calculates the volume of the now-closed surface model, and Step 1150 may store the volume measurement and/or landmark positions for future use. Once the volume measurement has been calculated, the surface model is no longer needed and may be discarded; the system. in some embodiments, may not store any surface model (or portion thereof), in order to preserve the privacy of the user. The routine exits at Step 1160.

Of note, measurement of a surface area of a portion of the user's body—as opposed to a volume measurement—may alternately be performed in Step 1130 by closing the surface model "with itself". In other words, if the surface model is envisioned as a very thin sheet or ribbon hugging the surface of the user's body, then the volume of the surface model is equivalent to an area of the surface of the body. In this way, FIG. 11 can be used to measure an area of the surface of the body as well as a volume of the body.

Figure 12:
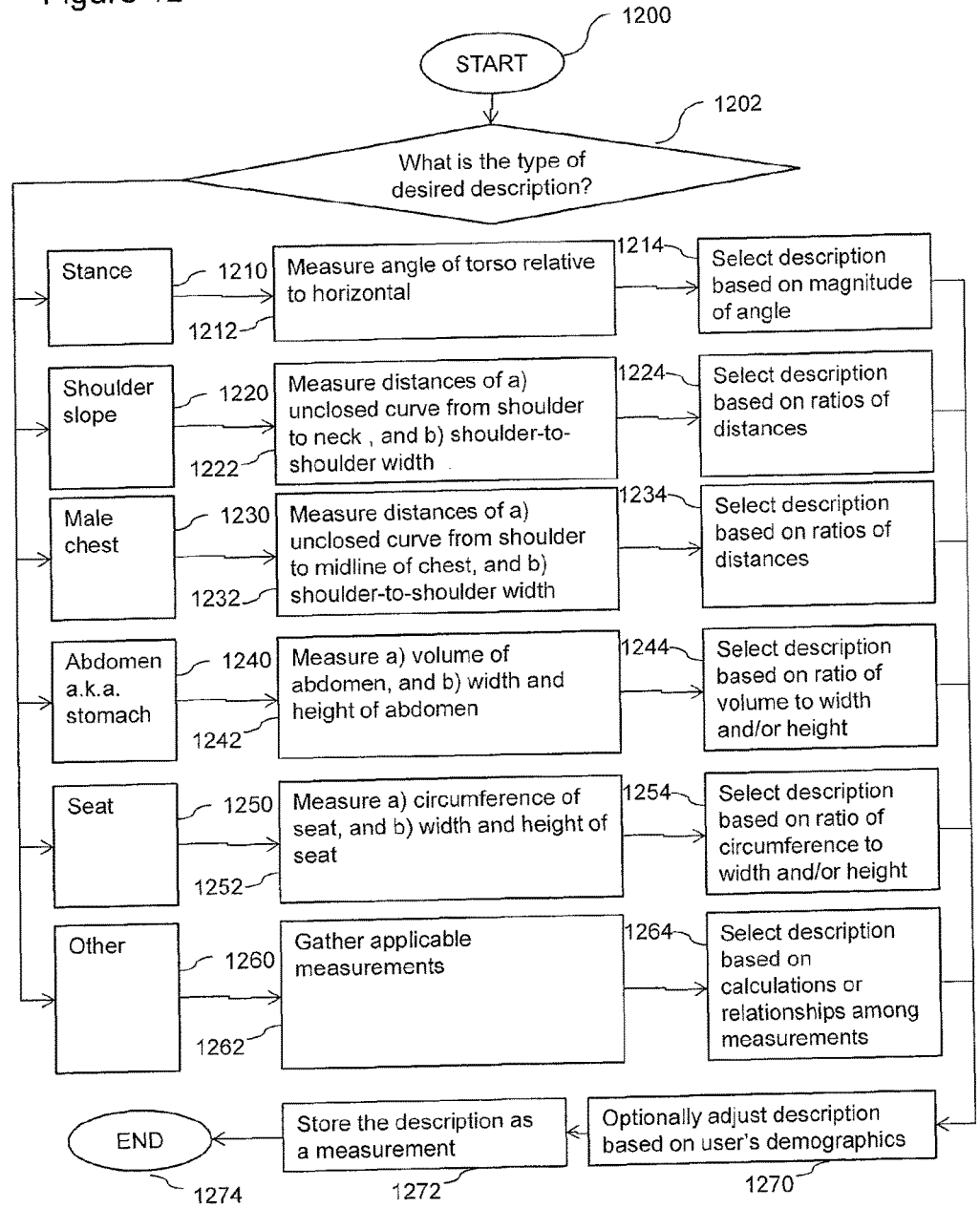
FIG. 12 shows a flowchart to obtain a qualitative description measurement according to a specific embodiment of the present method.

FIG. 12 is a flowchart showing the execution of a qualitative description measurement, beginning at step 1200. Step 1202 selects among the various types of descriptions. For a description of stance (e.g., normal, leaning, erect), Steps 1210 through 1214 measure the angle of the torso relative to horizontal, and select a description based on magnitude of the angle. (Note that stance may be either forward-backward or side-side, depending on the data-snapshot profile; this detail is omitted from FIG. 12 for brevity.) For a description of shoulder slope (e.g., normal, steep, flat), Steps 1220-1224 measure several distances related to the shoulder, and select a description based on the ratios of the distances.

For a description of male chest (e.g., thin, fit, normal, muscular, large), Steps 1230-1234 measure several distances related to the chest, and select a description based on the ratios of the distances. For a description of the abdomen a.k.a. stomach (e.g., thin, normal, medium large), Steps 1240-1244 measure the volume, width, and height of the abdomen, then select the description based on ratios of those measurements. For a description of the seat (e.g., normal, curved, large), Steps 1250-1254 measure several distances related to the seat, and select a description based on the ratios of the distances.

In general, for any description, as shown in Steps 1260-1264, a set of applicable measurements is first gathered, and then a description is selected based on various calculations or relationships among those measurements (e.g., using ratios). Step 1270 optionally adjusts the description based on user demographics (e.g., age or gender), and Step 1272 may store the description measurement for future use. The routine exits at Step 1274.

Figure 13:
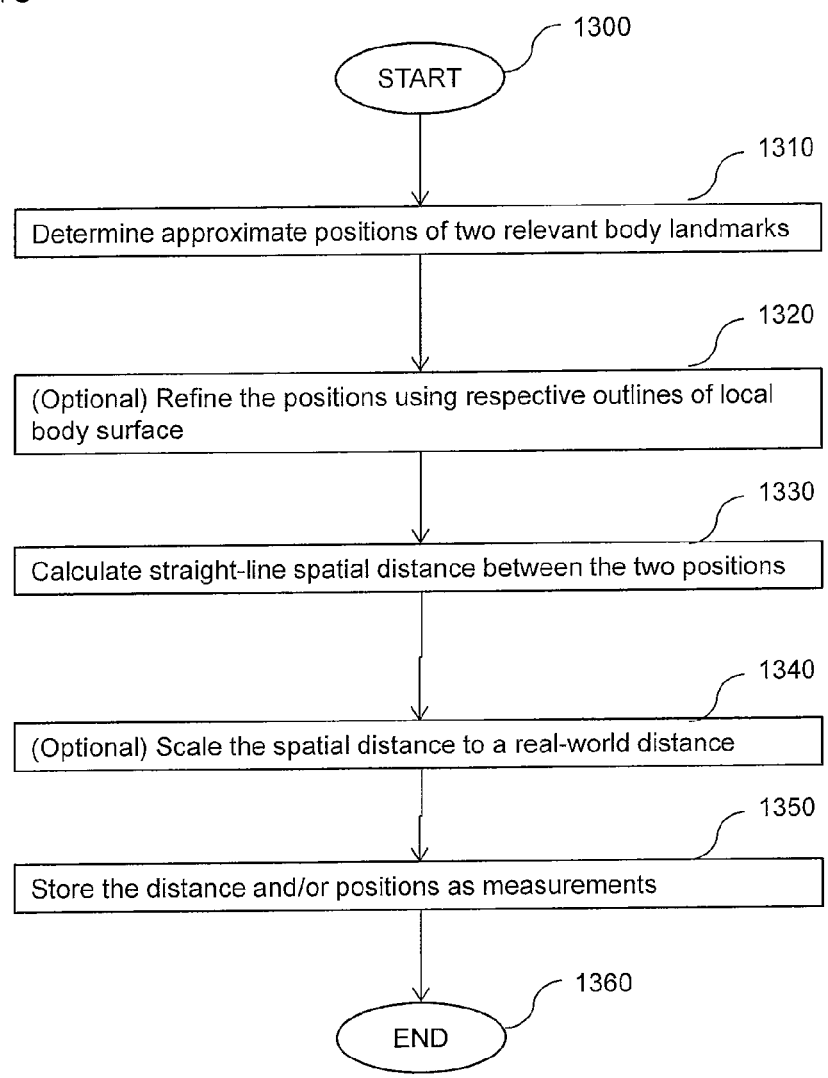
FIG. 13 shows a flowchart to obtain a distance between two body landmarks according to a specific embodiment of the present method.

FIG. 13 is a flowchart showing the execution of a measurement between two body landmarks, beginning at step 1300. As described earlier, each landmark may correspond to any distinguishing point (or set of points) on the user's body. For example, the two body landmarks might be the knees, so that FIG. 13 would result in a measurement of the knee-to-knee distance at a particular point in time. In Step 1310, the approximate spatial positions of each landmark are determined. In Step 1320, the approximate positions are optionally refined, using additional local body-surface data. In Step 1330, the straight-line spatial distance between the two landmark positions is calculated, and optionally scaled to a real-world distance in Step 1340. Step 1350 may store the distance and/or landmark positions as measurements, and Step 1360 exits the routine.

The measurements described across Steps 625 to 654 are not exhaustive. Additional types of measurements may be undertaken by the system 200. Examples of additional potential types of measurements include: the area of a portion of the body surface (e.g., the area that might be occupied by a tattoo); the point of steepest radial curvature of a line or surface along the body surface; and the minimum cross-sectional width or length of a body portion. Embodiments of the present system and method therefore may contemplate or conduct any kind of desired measurements of a user's body, and are not limited to the measurements described in FIG. 6.

FIG. 14, which begins at Step 1400, demonstrates the range of actions that may be performed once a collection of measurements, as described in FIG. 5 Step 505, is complete. For example, FIG. 5, Step 550, may invoke the steps of FIG. 14 one or more times. The actions that may be taken once measurements are gathered, as shown in FIG. 14, include:

Step 1405: store, adjust, or transmit the measurements or other parameters. For example, transmission of measurements may occur via the internet, to a clinical facility that can monitor the user for signs of health status decline; or locally, to a disk storage, so as to retain and chart measurements over time. Measurements or other parameters may also be adjusted, for example, to match requirements for data structure or for clinical use before being transmitted to another system or party. The term "parameter" herein refers to any aspect of the user, such as demographic data, or laboratory values from third-party devices (such as glucometers or blood pressure cuffs). (Note that in some embodiments, color image data 224, depth data 220, and optional skeleton data 222 are preferably not retained nor stored by the system 200, in order to preserve the privacy of the user.)

Step 1410: combine the measurements to generate new measurements, e.g., the height of the user may be calculated by summing the heights of head, torso, and leg, or the length of two contiguous unclosed curves that were obtained in different data-snapshots may be added together. For example, two approximately orthogonal straight-line measurements may be multiplied together to calculate the area of a portion of the body surface.

Step 1415: compare different measurements to improve the accuracy of the measuring process. As shown in FIG. 4, some measurements may be obtained across multiple user profiles (for example, upper-arm circumference might be measured in a front profile view, but also in a side profile view). Step 1415 may compare several measurements of the same part of the user's body, in order to improve the accuracy of a "composite" measurement: for example, by averaging two measurements of the same physical object taken from two different data-snapshots. Step 1415 may also perform an additional calibration check on the system as a whole, by taking measurements of known objects using different data-snapshots, and then comparing the measurements to check for consistency.

Step 1420: compare or contrast measurements over time. This allows measurements to be charted or trended over time, looking for signals of health status decline. For example, a decrease in stride length over time, or a stooping of posture over time, may signal health status deterioration.

Step 1425: compare the measurements of Steps 535 and 540 to the baseline of Step 530, or to other comparators (for example, average measurement values for the wider population of individuals with similar age, height, weight, and gender). Step 1425 may perform comparisons using thresholds, statistical methods, or any other methods that enable a comparison of measurements over space or time.

The routine exits at Step 1450.

The actions listed in FIG. 14 may be combined in any number, order, or sequence, and are further not intended to be exhaustive. The scope of the system includes any actions that may be performed upon the gathered measurements.

Figure 15:
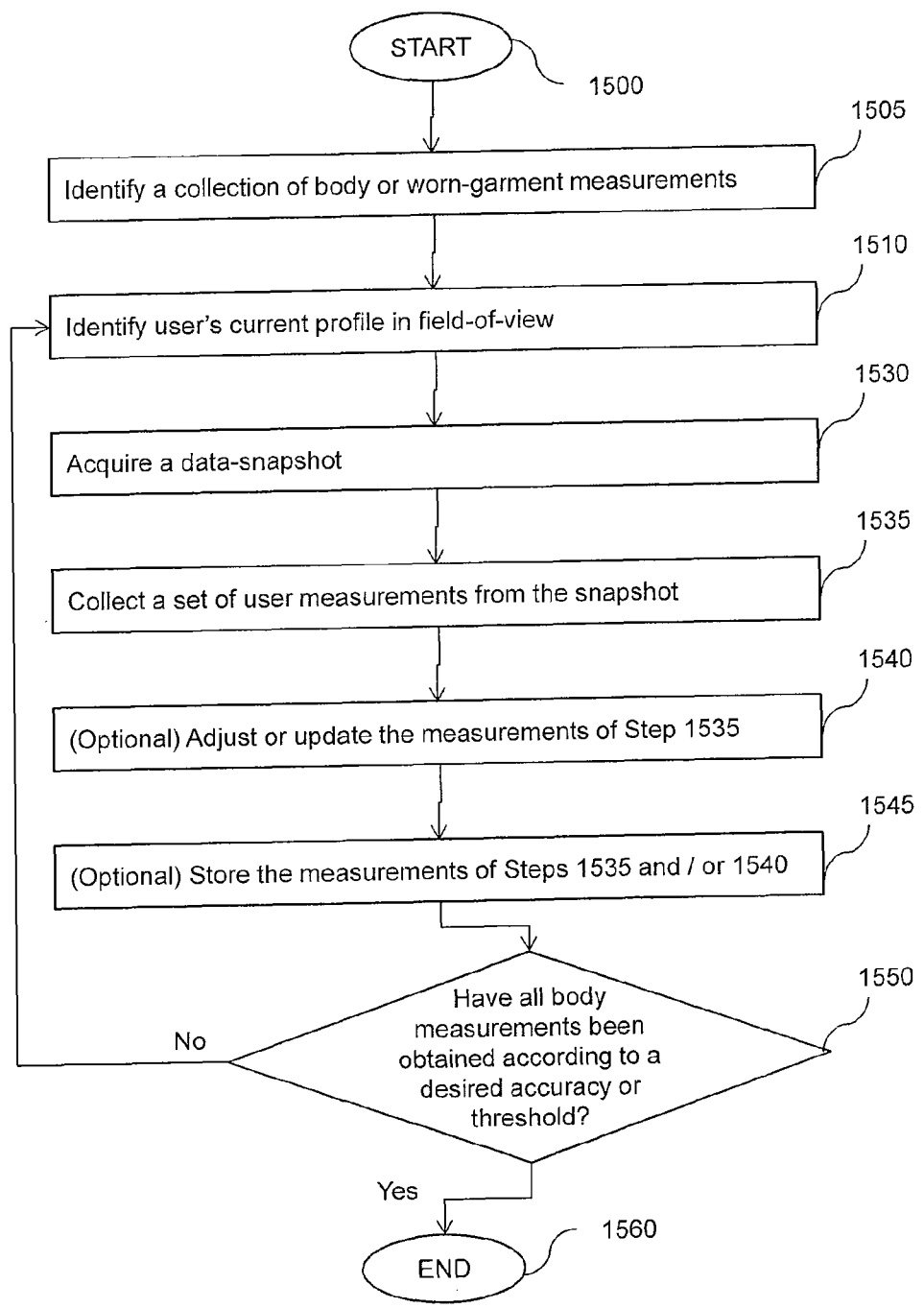
FIG. 15 shows a high-level flowchart according to another specific embodiment of the present method.

FIG. 15 shows a high-level flowchart describing a preferred embodiment of the present system and method, beginning at step 1500. Similar to FIG. 6, the purpose of the process shown in FIG. 15 is to enable detection of deterioration of health status without the requirement for a user to pose or stay still for a lengthy period of time. In other words, the goal of FIG. 15 is to opportunistically acquire measurements in real-time, while the user moves around naturally. In Step 1505, a collection of body measurements is identified, as described previously.

In Step 1510, the user's current profile is determined. For example, if the user happens to be facing the sensor portion 201 straight-on, then the current profile is a front profile; or, if the user happens to be turned sideways to the sensor portion 201, then current profile is a side profile. There are many different ways to determine the user's current profile.

For example, one way is to evaluate the relative approximate positions of the user's joints, such as shoulders and knees, relative to each other and/or to the sensor portion 201. For example, another way is to apply facial recognition technologies to find the user's face and, if found, estimate the angle of the face relative to the sensor portion 201.

Optionally, the detected profile may be communicated to the user in Step 1510, or at any other point in FIG. 15. For example, a screen display may indicate to the user that system 200 has identified the user to be in (for example) front profile. The user may then respond or adjust to the detected profile. For example, if the user intends to present a side profile to system 200, but the system 200 erroneously detects a front profile, the user is given an opportunity to become aware of the error, and may adjust his/her position and stance to aid system 200 in detecting the correct profile.

Once the user's profile has been determined, a data-snapshot is acquired in Step 1530, and a set of measurements is collected in Step 1535, as described previously.

Next, in Step 1540, the measurements from Step 1535 are optionally adjusted or updated. For example, to measure the shoulder-to-shoulder width of the user, the system 200 might perform a series of measurements over time—during which the apparent shoulder-to-shoulder width may vary widely, as the user alternately faced the camera, or turned so present a side view to the camera. The process would then retain the largest such measurement under the assumption that the widest shoulder-to-shoulder measurement acquired by the system 200 would best match the real-world shoulder-to-shoulder distance.

Alternatively, the system 200 may calculate a running average of measurements, for example, by averaging the most-recent 100 measurements of the length of the left arm, so as to dampen signal noise. The purpose of Step 1540, essentially, is to compensate for ongoing motions or varied stances of the user, so that measurements may be acquired or refined opportunistically, even while the user moves about naturally.

In Step 1545, the results of Steps 1535 and/or 1540 may be stored for further use. For example, if averaging certain measurements over time is desired, as described above, then Step 1545 may be responsible for maintaining a stored series of measurements so that the running average may be calculated.

Optionally, the obtained measurements may be communicated to the user in Step 1545, or at any other point in FIG. 15. For example, a screen display may indicate to the user that system 200 has measured the user's stride length to be (for example) 12 inches. Or, for example, a screen display may draw rendered "virtual health status updates" superimposed on an image of the user's body, thus indicating graphically some of the underlying calculations leading to the obtained measurements. The user may then respond or adjust to the obtained measurements.

Thus the system 200 and the user may adjust and respond to each other, interactively, in real-time. This interactivity applies whether the user is moving or stationary, as in both cases, the system 200 may continue to acquire data snapshots on an ongoing basis (for example, at a rate of 30 snapshots per second).

If graphical representations are employed by system 200, then to safeguard the user's privacy, it may be desirable to avoid displaying an image of the user's face or head, while preserving the remainder of the user's body and the communication of measurements. For example, if body measurements are communicated to the user graphically by draping "virtual health status updates" onto an image of the user's body, then before displaying the graphical representation, the system 200 may identify the portion of the user's body that represents the face or the head, and "blank out" or delete the visual information corresponding to that portion. In this way, the user's privacy may be safeguarded when needed.

As noted previously, in some embodiments, the system 200 may not gather any color image information at all. In other embodiments, the system 200 may gather color image information only temporarily, in order to use the color image information to carry out a set of measurements, and then immediately afterward discard the color image information. In general, for applications where user privacy is important, it is preferable to either gather no color image data at all; or, if color image data is required for some measurements, to gather color image data only as long as needed to determine the measurements, and then discard the color image data as soon as possible, without further storing or transmitting the color image data.

Step 1550 then checks whether all body measurements have been obtained, to a desired level of accuracy or threshold, and if so, Step 1560 exits the process. For example, Step 1550 might transition to exit if the set of measurements in Step 1545 remains constant within (for example) $1/10$ of a centimeter during (for example) 60 contiguous measurements. For example, Step 1550 might transition to exit if the user views a set of measurements on a display screen and chooses to stop acquiring new measurements. Although not shown in FIG. 15 for reasons of brevity, it is appreciated that other decision points, besides Step 1550, are possible and would fall within the scope of the present system and method. In some embodiments of the present inventive method, Step 1550 does not exit, but instead may execute indefinitely (for example, to supply ongoing, long-term monitoring in a user's home).

For example, if the system 200, in following the steps of FIG. 15, failed to opportunistically find all necessary body measurements within an elapsed period of time (say, five minutes), which could occur, for example, if the user did not move about sufficiently to present the prerequisite profiles of FIG. 4 to the sensor portion 201, then the system 200 could optionally prompt the user to assume the prerequisite profile.

Figure 16A:
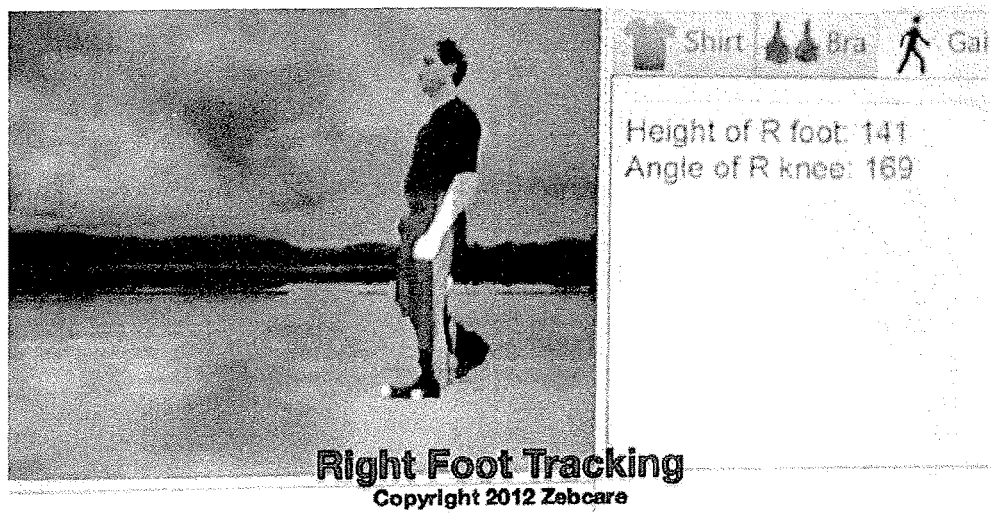
FIGS. 16A and 16B show screenshot examples of a real-world embodiment of the present system and method.
Figure 16B:
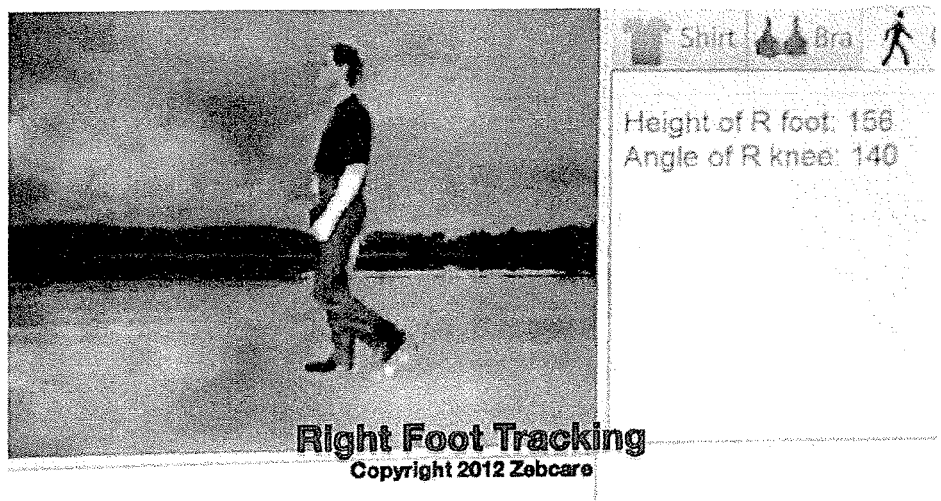

FIGS. 16A and 16B show screenshot examples of a real-world embodiment of the present inventive method. The application in this example is gait analysis. FIG. 16A corresponds to an early pass through the process steps illustrated in the flowchart of FIG. 15. In FIG. 16A, a user has been identified in the field-of-view of system 200, and the system has begun acquiring a set of predetermined landmarks along the right foot, that are relevant to the application of gait analysis.

The brightly colored dots in FIG. 16A are "virtual health status updates" indicia, that is, graphical representations of the system's measurement progress, which may be updated and displayed to the user, or to another person (such as a clinician), in real-time. As the user moves about in real-time, the "virtual health status updates" follow the user's motion, also in real-time. FIG. 16B corresponds to a later time through the process steps illustrated in the flowchart of FIG. 15. In this example, Step 1550 in FIG. 15 loops indefinitely, without exiting.

The relationship of derivative body measurements to the three primary profiles is shown in FIG. 17. Recall that FIG. 4 shows the relationship of direct body measurements to the three primary profiles. Derivative measurements are measurements that are calculated, indirectly, from the direct measurements of the user's body, possibly over time. For each derivative measurement shown in FIG. 17, the "preferred profile" is the first-choice profile of the user with which to conduct that measurement, and the "alternate profile" is a backup choice that may be used in place of (or in addition to) the preferred profile. Many of the derivative measurements in FIG. 17 require a series of direct measurements taken over time; for example, time per day spent standing would require a series of posture measurements over time each day, to estimate how much time the user spent standing as opposed to sitting or lying down.

Figure 18A:
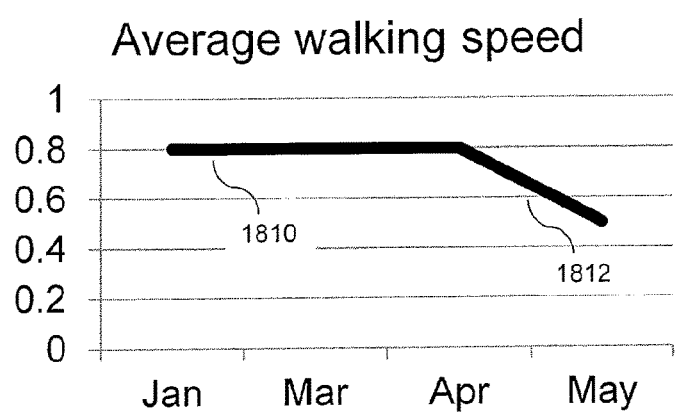
FIGS. 18A and 18B show examples of analytics that may be performed by embodiments of the present system and method.
Figure 18B:
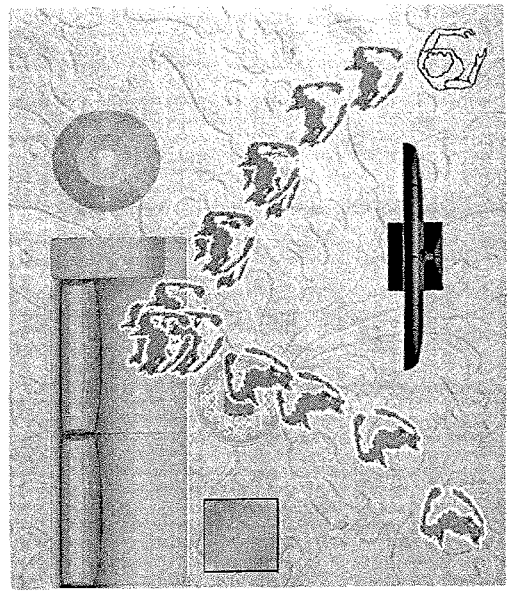

FIGS. 18A and 18B show illustrative examples of analytics that may be performed upon the spatial measurements obtained by the system 200. FIG. 18A shows a series of measurements of an individual's walking speed over several months. In this example, a decline in the individual's walking speed is detected by system 200. In this example, system 200 first established a measurement baseline 1810 corresponding to the flat portion of the curve in FIG. 18A. Subsequently, system 200 detected that the user's walking speed measurements were exhibiting a deviation from baseline 1812. FIG. 18B shows a "heat map" of an individual's location within a room, displaying widely-spaced representations of the individual where he/she spends less time, and closer-spaced representations where he/she spends more time. Such a heat map demonstrates, for example, that over time, an individual was spending increasingly more time sitting on a couch, and less time actively walking around. (Baseline and deviation measurements are not explicitly shown in FIG. 18B.)

As mentioned earlier, embodiments of the present inventive method may be used in a wide variety of applications. For example, in detecting deterioration of health status, embodiments of the present inventive method may be employed to measure walking speed; the time required to stand up or sit down; degree of ankle dorsiflexion; location within a room; and many other types of body surface measurements. These are illustrative examples and do not restrict the scope of the present inventive method.

Returning to FIGS. 2A-2F, the system 200 may be embodied as a system cooperating with computer hardware components and/or as computer-implemented methods. The system 200 may include a plurality of software modules or subsystems. The modules or subsystems, such as the sensor portion 201 and the computer subsystem 298, may be implemented in hardware, software, firmware, or any combination of hardware, software, and firmware, and may or may not reside within a single physical or logical space. For example, the modules or subsystems referred to in this document and which may or may not be shown in the drawings, may be remotely located from each other and may be coupled by a communication network.

The system 270 of FIG. 2F is a high-level hardware block diagram of one embodiment of the system 200 used to detect deterioration of health status. The system 200 may be embodied as a system cooperating with computer hardware components and/or as computer-implemented methods. For example, the subsystems, such as the depth calculation module 210 and all other modules herein, may each include a plurality of software modules or subsystems. The modules or subsystems may be implemented in hardware, software, firmware, or any combination of hardware, software, and firmware, and may or may not reside within a single physical or logical space. For example, the modules or subsystems referred to in this document and which may or may not be shown in the drawings, may be remotely located from each other and may be coupled by a communication network.

Additionally, the hardware system 200 shown in FIGS. 2A-2F, including the various cameras and sensors, in one specific embodiment may be provided by one or more commercially-available hardware platforms. For example, sensor portion 201 may be provided by the Kinect System, available from Microsoft Corporation, or by the Xtion device, available from Asus Corporation. Such commercially available devices may be used to generate depth data and/or color image data and/or skeleton data and/or pixel label data. For example, computer subsystem 298 may be provided by the Xbox System, available from Microsoft Corporation, or by a personal computer, such as one running Microsoft Windows or Apple OS X.

Furthermore, FIG. 2F displays a high-level hardware block diagram of a system computer 298 that may be used to execute software or logic to implement the measurements of the user and other steps disclosed in this document. The computer or computer subsystem 298 may be a personal computer and may include or connect to various hardware components, such as the RAM 296, the ROM 297, the data storage 284, and the like. The computer 298 may include any suitable processor or processing device 295, such as a subsystem computer, microprocessor, RISC processor (reduced instruction set computer), CISC processor (complex instruction set computer), mainframe computer, work station, single-chip computer, distributed processor, server, controller, micro-controller, discrete logic computer, and the like, as is known in the art.

For example, the processing device 295 may be an Intel Pentium® microprocessor, x86 compatible microprocessor, single core processor, dual-core processor, multi-core processor, or equivalent device, and may be incorporated into a server, a personal computer, server, remote computer, cloud processing platform, or any suitable computing platform.

The RAM 296 and ROM 297 may be incorporated into a memory subsystem, which may further include suitable storage components, such as RAM, EPROM (electrically programmable ROM), flash memory, dynamic memory, static memory, FIFO (first-in, first-out) memory, LIFO (last-in, first-out) memory, circular memory, semiconductor memory, bubble memory, buffer memory, disk memory, optical memory, cache memory, and the like. Any suitable form of memory may be used, whether fixed storage on a magnetic medium, storage in a semiconductor device, or remote storage accessible through a communication link. A user input 287 may be coupled to the computer 298 and may include various input devices, such as switches selectable by the system manager and/or a keyboard, or may be conducted independently of such devices, e.g., by using hand gestures or other body gestures, or by using voice commands. The user interface also may include suitable display devices 285, such as an LCD display, a CRT, various LED indicators, a printer, and/or a speech output device, as is known in the art.

To facilitate communication between the computer 298 and external sources, a communication interface 286 may be operatively coupled to the computer system. The communication interface 286 may be, for example, a local area network, such as an Ethernet network, intranet, Internet, or other suitable network. The communication interface 286 may also be connected to a public switched telephone network (PSTN) or POTS (plain old telephone system), which may facilitate communication via the Internet. Any suitable commercially-available communication device or network may be used.

The logic, circuitry, and processing described above may be encoded or stored in a machine-readable or computer-readable medium such as a compact disc read only memory (CDROM), magnetic or optical disk, flash memory, random access memory (RAM) or read only memory (ROM), erasable programmable read only memory (EPROM) or other machine-readable medium as, for examples, instructions for execution by a processor, controller, or other processing device.

The medium may be implemented as any device that contains, stores, communicates, propagates, or transports executable instructions for use by or in connection with an instruction executable system, apparatus, or device. Alternatively or additionally, the logic may be implemented as analog or digital logic using hardware, such as one or more integrated circuits, or one or more processors executing instructions; or in software in an application programming interface (API) or in a Dynamic Link Library (DLL), functions available in a shared memory or defined as local or remote procedure calls; or as a combination of hardware and software.

In other implementations, the logic may be represented in a signal or a propagated-signal medium. For example, the instructions that implement the logic of any given program may take the form of an electronic, magnetic, optical, electromagnetic, infrared, or other type of signal. The systems described above may receive such a signal at a communication interface, such as an optical fiber interface, antenna, or other analog or digital signal interface, recover the instructions from the signal, store them in a machine-readable memory, and/or execute them with a processor.

The systems may include additional or different logic and may be implemented in many different ways. A processor may be implemented as a controller, microprocessor, microcontroller, application specific integrated circuit (ASIC), discrete logic, or a combination of other types of circuits or logic. Similarly, memories may be DRAM, SRAM, Flash, or other types of memory. Parameters (e.g., conditions and thresholds) and other data structures may be separately stored and managed, may be incorporated into a single memory or database, or may be logically and physically organized in many different ways. Programs and instructions may be parts of a single program, separate programs, or distributed across several memories and processors.

Returning to FIG. 14, Step 1405 enables the user of the system to store, adjust, and/or transmit measurements or other parameters. These stored, adjusted, and/or transmitted items may be determined by the most recent set of measurements conducted by the system 200; or by any previous set of measurements, conducted by the system 200 in the past, and then stored for later use; or by any set of measurements provided exogenously (e.g., through ancillary devices or user input); or by any combination of subsets thereof, including any combination of individual measurements drawn across different collections of measurements, including measurements acquired by the system 200 or supplied by the user or by other sources.

The system 200 may interface with, or interact with, an online portal through which people may view historic and current measurements, and analytics on those measurements (for example, graphs or calculations). The portal may be a web browser portal, or a portal that is made available through a software download to a videogame system, or a portal that is made available through an application download to a tablet computer or a mobile phone, or any other type of online shopping interface.

Examples of commercially-available web browsers include Microsoft Internet Explorer, Mozilla Firefox, Apple Safari, and Google Chrome. Examples of commercially-available videogame systems include Microsoft Xbox, Sony PlayStation 3, and Nintendo Wii. Examples of tablet computers include Apple iPad and Samsung Galaxy Tab. Examples of mobile phone operating systems include Microsoft Windows Phone, Apple iPhone iOS, and Google Android. Embodiments of the present system and method may incorporate, link to, network with, transmit information to or from, or otherwise employ or utilize any kind of online portal, whether part of the system 200 or supplied by a third party, without limitation.

In Step 1405, the system 200 may transmit measurements or other parameters, for example, to subsystems of system 200 (such as data storage device 284), or to external systems or recipients (such as a clinical facility or online database). The measurements or other parameters may be adjusted in terms of format, units (e.g. metric vs. imperial), or in any way desired. The measurements or other parameters may be transmitted to, from, or via an online portal, or to, from, or via any other system or third party. A recipient of measurements or other parameters may be, for example, a clinician, who evaluates whether a health status decline is likely occurring, and who may choose to intervene, for example, by calling or visiting the patient.

A recipient of measurements or other parameters may also be a caregiver, such as a relative or home aide or friend. A recipient of measurements or other parameters may also be a social networking system, such as a website or mobile application, which may be part of the system 200 or may be provided by or via any other system or third party, and which may utilize the measurements or other parameters to share the user's health status with other individuals in the user's social network.

Returning back to FIG. 3A, system 300 incorporates all aspects of the system 200, but augmented with audio sensor 308 and output audio data 309. For example, audio sensor 308 may be a microphone or an array of microphones. System 300 is therefore capable of conducting measurements of the user's voice and speech, in addition to measurements of the user's body. For example, system 300 may conduct measurements of the volume and cadence of the user's speech over time. For example, reduced volume compared to baseline, or slurred speech compared to population comparators, may indicate a decline in health status. Measurements of the user's voice may also be undertaken to evaluate emotional status—for example, louder volume than usual, or frequency spectra consistent with angry or depressed tones of voice. References to "measurements" contained herein therefore may therefore refer not just to spatial measurements of a user's body, but also audio measurements of the user's voice and speech.

While various embodiments of the invention have been described, it will be apparent to those of ordinary skill in the art that many more embodiments and implementations are possible within the scope of the invention. Accordingly, the invention is not to be restricted except in light of the attached claims and their equivalents.

What is claimed is:

1. A method of monitoring a health status of an individual, the method comprising:
   providing, by an energy emitter, over a period of time, energy within a field-of-view for generating a depth map of the field-of-view;
   capturing, by an energy sensor, over the period of time, energy reflected from an individual positioned within the field-of-view;
   generating, by a processor of a computing device, depth data for the field-of-view based on the captured data from the energy sensor;
   at each of a plurality of instances within the period of time, determining, by the processor, a user profile of the individual based at least in part on the generated depth data for the field-of-view, wherein the user profile is a view that the individual presents to the energy sensor at the corresponding instance, wherein the view that the individual presents to the energy sensor is a member selected from the group consisting of a front profile, a side profile, and a back profile;
   at each of the plurality of instances within the period of time, selecting, by the processor, one or more direct measurements from a predetermined set of direct measurements of a body of the individual to perform based on the user profile of the individual at the corresponding instance and determining, by the processor, the one or more selected direct measurements of the body of the individual using the generated depth data for the field-of-view at the corresponding instance, thereby repeatedly selecting and determining one or more direct measurements over the period of time in order to track the health status of the individual over time;
   determining, by the processor, a plurality of derivative measurements indicative of the health status based at least in part on the one or more direct measurements, wherein the plurality of derivative measurements are repeatedly determined over a period of time in order to track the health status of the individual over time, wherein:
      the plurality of derivative measurements comprise measurements that indicate (i) whether the individual is sitting and (ii) a walking speed of the individual, and said determining the plurality of derivative measurements comprises:
         determining, by the processor, whether the individual is sitting based at least in part on the one or more direct measurements;
         determining, by the processor, a first location of at least a portion of a body part of the individual at a first time based at least in part on the one or more direct measurements;
         determining, by the processor, a second location of at least a portion of the body part of the individual at a second time based at least in part on the one or more direct measurements; and
         determining, by the processor, the walking speed of the individual based at least in part on a distance between the first location and the second location and a difference between the first time and the second time;
   storing in a database, by the processor, at least a portion of the one or more direct measurements and the plurality of derivative measurements such that historic measurements are stored for the individual for use in monitoring the health status of the individual; and
   displaying, in real time, the plurality of derivative measurements.

2. The method of claim 1, wherein the data captured corresponding to the individual within the field-of-view is captured in real-time while the individual moves about in real-time.

3. The method of claim 1, wherein the health status of the individual is monitored without acquiring visual-light images or video.

4. The method of claim 1, wherein:
   the energy emitted by the energy emitter comprises a pattern of emitted energy,
   the energy detected by the energy sensor comprises a pattern of reflected energy, and
   the depth data for the field-of-view is generated based a difference between the pattern of the emitted energy and the pattern of reflected energy.

5. The method of claim 1, wherein
   the depth data for the field-of-view is generated based a difference between a phase of the emitted energy and a phase of captured energy.

6. The method of claim 1, comprising:
   establishing a first portion of the plurality of derivative measurements as baseline measurements for the individual; and
   comparing a second portion of the plurality of derivative measurements against the baseline measurements to detect deviations in the health status of the individual.

7. The method of claim 1, wherein measurements stored in the database are accessible via an online portal wherein the historic measurements for the individual are viewable, wherein an amount of time the individual is sitting and the walking speed of the individual over time are compared to baseline measurements to determine the health status of the individual.

8. The method of claim 1, wherein the one or more direct measurements comprise one or more members selected from the group consisting of an angle of left- or right-leaning body relative to horizontal, an angle of forward- or backward-leaning body relative to horizontal, an angle of head-and-neck relative to torso, an angle of head-and-neck relative to torso, an angle of torso relative to legs, a position of hand relative to shoulder, a position of hand relative to other hand, a position of knee relative to hip, a position of knee relative to other knee, a tip of foot, a back of heel, a bottom of sole of foot, a position of foot relative to hip, a position of foot relative to other foot, and a position of head relative to floor.

9. The method of claim 1, wherein the plurality of derivative measurements comprises one or more members selected from the group consisting of a rotation of upper body relative to lower body, a maximum distance between two feet during a stride, a maximum distance between hand and torso during a stride, a maximum angle of rotation at shoulder during a stride, a speed of locomotion, a stride distance of locomotion, a frequency of locomotion, average and/or maximum acceleration of hand and/or foot, a qualitative estimate of stance, a time per day spent standing, a time per day spent walking, and a time per day spent sitting.

10. A system for monitoring a health status of an individual, comprising:
   at least one energy emitter for emitting energy within a field of view for generating a depth map of the field-of-view;
   at least one energy sensor for capturing energy reflected from the individual positioned within the field of view; and a computing device comprising a processor and a memory storing instructions thereon, that when executed by the processor, cause the processor to:

generate, over a period of time, depth data for the field-of-view based on the captured data from the at least one energy sensor;

at each of a plurality of instances within the period of time, determine a user profile of the individual based at least in part on the generated depth data for the field-of-view, wherein the user profile is a view that the individual presents to the energy sensor at the corresponding instance, wherein the view that the individual presents to the energy sensor is a member selected from the group consisting of a front profile, a side profile, and a back profile;

at each of the plurality of instances within the period of time, select one or more direct measurements from a predetermined set of direct measurements of a body of the individual to perform based on the user profile of the individual at the corresponding instance and determine the one or more selected direct measurements of the body of the individual using the generated depth data for the field-of-view at the corresponding instance to track the health status of the individual over time;

determine a plurality of derivative measurements indicative of the health status based at least in part on the one or more direct measurements, wherein the plurality of derivative measurements are repeatedly determined over a period of time in order to track the health status of the individual over time, wherein:

the plurality of derivative measurements comprise measurements that indicate (i) whether the individual is sitting and (ii) a walking speed of the individual, and said determining the plurality of derivative measurements comprises:

determining the-whether the individual is sitting based at least in part on the one or more direct measurements;

determining a first location of at least a portion of a body part of the individual at a first time based at least in part on the one or more direct measurements;

determining a second location of at least a portion of the body part of the individual at a second time based at least in part on the one or more direct measurements; and determining the walking speed of the individual based at least in part on a distance between the first location and the second location and a difference between the first time and the second time;

store, in a database, at least a portion of the one or more direct measurements and the plurality of derivative measurements such that historic measurements are stored for the individual for use in monitoring the health status of the individual; and display, in real time, the plurality of derivative measurements.

11. The system of claim 10, wherein the instructions stored on the memory, when executed by the processor, cause the processor to compare at least a portion of the plurality of derivative measurements against baseline measurements for the individual to detect deviations indicative of a deviation in health status, wherein the baseline measurements comprise a portion of the plurality of derivative measurements.

12. The system of claim 10, wherein
the energy emitted by the at least one energy emitter comprises a pattern of emitted energy,
the energy detected by the at least one energy sensor comprises a pattern of reflected energy, and
the depth data for the field-of-view is generated based a difference between the pattern of the emitted energy and the pattern of reflected energy.

13. The system of claim 10, wherein the instructions stored in the memory, when executed by the processor, cause the processor to extract skeleton data from the generated depth data.

14. The system of claim 13, wherein the plurality of derivative measurements are determined based at least in part on a combination of the generated depth data and the extracted skeleton data.

15. The system of claim 10, the system comprising a visible light energy sensor configured to acquire visible light.

16. The system of claim 15, wherein the plurality of derivative measurements are determined based at least in part on a combination of the generated depth data and data corresponding to the acquired visible light.

17. The system of claim 10, wherein the energy emitted by the energy emitter is infrared light and the reflected energy captured by the energy sensor is reflected infrared light.

18. The system of claim 10, wherein the system monitors the health status of the individual without acquiring visual-light images or video.

19. The system of claim 10, wherein
the depth data for the field-of-view is generated based a difference between a phase of the emitted energy and a phase of captured energy.

20. The system of claim 10, wherein measurements stored in the database are accessible via an online portal wherein the historic measurements for the individual are viewable, wherein an amount of time the individual is sitting and the walking speed of the individual over time are compared to baseline measurements to determine the health status of the individual.

21. The system of claim 10, wherein the one or more direct measurements comprise one or more members selected from the group consisting of an angle of left- or right-leaning body relative to horizontal, an angle of forward- or backward-leaning body relative to horizontal, an angle of head-and-neck relative to torso, an angle of head-and-neck relative to torso, an angle of torso relative to legs, a position of hand relative to shoulder, a position of hand relative to other hand, a position of knee relative to hip, a position of knee relative to other knee, a tip of foot, a back of heel, a bottom of sole of foot, a position of foot relative to hip, a position of foot relative to other foot, and a position of head relative to floor.

22. The system of claim 10, wherein the plurality of derivative measurements comprises one or more members selected from the group consisting of a rotation of upper body relative to lower body, a maximum distance between two feet during a stride, a maximum distance between hand and torso during a stride, a maximum angle of rotation at shoulder during a stride, a speed of locomotion, a stride distance of locomotion, a frequency of locomotion, average and/or maximum acceleration of hand and/or foot, a qualitative estimate of stance, a time per day spent standing, a time per day spent walking, and a time per day spent sitting.

23. A method of monitoring a health status of an individual, the method comprising:

receiving, by a processor of a computing device, over a period of time, depth data for a field-of-view of an energy sensor, wherein the depth data has been generated based on energy emitted or reflected from the individual that is captured by the energy sensor when the individual is within the field-of-view of the energy sensor;

at each of a plurality of instances within the period of time, determining, by the processor, a user profile of the individual based at least in part on the received depth data for the field-of-view, wherein the user profile is a view that the individual presents to the energy sensor at the corresponding instance, wherein the view that the individual presents to the energy sensor is a member selected from the group consisting of a front profile, a side profile, and a back profile;

at each of the plurality of instances within the period of time, selecting, by the processor, one or more direct measurements from a predetermined set of direct measurements of a body of the individual to perform based on the user profile of the individual at the corresponding instance and determining, by the processor, the one or more selected direct measurements of the body of the user using the received depth data for the field-of-view, thereby repeatedly selecting and determining one or more direct measurements over the period of time in order to track the health status of the individual;

determining, by the processor, a plurality of derivative measurements indicative of the health status of the individual over time based at least in part on the one or more direct measurements, wherein the plurality of derivative measurements are repeatedly determined over a period of time to track the health status of the individual, wherein the plurality of derivative measurements comprise measurements that indicate (i) whether the individual is sitting and (ii) a walking speed of the individual;

storing in a database, by the processor, at least a portion of the plurality of direct measurements and the plurality of derivative measurements such that historic measurements are stored for the individual for use in monitoring the health status of the individual; and displaying, in real time, the plurality of derivative measurements.

24. The method of claim 23, the method comprising:
prompting the individual to assume a particular user profile.

25. The method of claim 23, the method comprising:
determining, by the processor, a change in the user profile to a second user profile;

determining, by the processor, one or more new direct measurements based at least in part on the second user profile, wherein the one or more new direct measurements are repeatedly determined over a period of time to track the health status of the individual and the one or more new direct measurements are different measurements from the one or more direct measurements;

determining, by the processor, a plurality of derivative measurements indicative of the health status based at least in part on the one or more new direct measurements, wherein the plurality of derivative measurements are repeatedly determined over a period of time in order to track the health status of the individual over time;

storing in a database, by the processor, a portion of the plurality of derivative measurements wherein historic measurements are stored for the individual for use in monitoring the health status of the individual; and displaying, in real time, the plurality of derivative measurements.

26. The method of claim 23, wherein the energy reflected from the individual is reflected ambient light or reflected energy that has been emitted by an energy emitter.

* * * * *

UNITED STATES PATENT AND TRADEMARK OFFICE
CERTIFICATE OF CORRECTION

PATENT NO. : 9,974,466 B2
APPLICATION NO. : 14/352305
DATED : May 22, 2018
INVENTOR(S) : Zebediah M. Kimmel It is certified that error appears in the above-identified patent and that said Letters Patent is hereby corrected as shown below:

In the Claims

1. In Claim 4 (Column 36, Line 15), please delete "based a" and replace with --based on a-- therefor.

2. In Claim 5 (Column 36, Line 19), please delete "based a" and replace with --based on a-- therefor.

3. In Claim 10 (Column 37, Line 38), please delete "the-whether" and replace with --whether-- therefor.

4. In Claim 12 (Column 38, Line 6), please delete "based a" and replace with --based on a-- therefor.

5. In Claim 19 (Column 38, Line 32), please delete "based a" and replace with --based on a-- therefor.

Signed and Sealed this
Thirty-first Day of July, 2018

Andrei Iancu
*Director of the United States Patent and Trademark Office*